United States Patent [19]

Horwell et al.

[11] Patent Number: 5,264,419
[45] Date of Patent: Nov. 23, 1993

[54] N-SUBSTITUTED CYCLOALKYL AND POLYCYCLOALKYL α-SUBSTITUTED TRP DERIVATIVES

[75] Inventors: David C. Horwell, Foxton; Martyn C. Pritchard, Swavesey; Edward Roberts, Wood Ditton, all of England

[73] Assignee: Warner-Lambert Company, Morris Plains, N.J.

[21] Appl. No.: 726,652

[22] Filed: Jul. 12, 1991

Related U.S. Application Data

[63] Continuation-in-part of Ser. No. 576,024, Aug. 31, 1990, abandoned.

[51] Int. Cl.⁵ .............. A61K 37/02; C07K 5/06; C07K 5/08
[52] U.S. Cl. .................................. 514/18; 514/19; 530/331; 548/253; 548/409; 548/411; 548/469
[58] Field of Search ............ 530/331; 514/18, 19; 548/253, 409, 411, 469

[56] References Cited

U.S. PATENT DOCUMENTS

| | | | |
|---|---|---|---|
| 4,757,151 | 7/1988 | Horwell | 548/469 |
| 5,010,076 | 4/1991 | Waldeck et al. | 514/221 |

*Primary Examiner*—Lester L. Lee
*Attorney, Agent, or Firm*—Elizabeth M. Anderson

[57] ABSTRACT

Novel peptoids of α-substituted Trp derivatives useful as agents in the treatment of obesity, hypersecretion of gastric acid in the gut, gastrin-dependent tumors, or as antipsychotics are disclosed. Further the compounds are antianxiety agents and antiulcer agents. They are agents useful for preventing the response to withdrawal from chronic treatment or use of nicotine, diazepam, alcohol, cocaine, caffeine, or opioids. The compounds are also useful in the treatment and/or prevention of panic attacks. Also disclosed are pharmaceutical compositions and methods of treatment using the peptoids as well as processes for preparing them and novel intermediates useful in their preparation. An additional feature of the invention is the use of the subject compounds to prepare diagnostic compositions.

11 Claims, No Drawings

N-SUBSTITUTED CYCLOALKYL AND POLYCYCLOALKYL α-SUBSTITUTED TRP DERIVATIVES

This is a continuation-in-part application of U.S. Ser. No. 07/576,024, filed Aug. 31, 1990 and now abandoned.

BACKGROUND OF THE INVENTION

Agents acting at central cholecystokinin (CCK) receptors may induce satiety (Schick, Yaksh and Go, *Regulatory Peptides* 14:277–291, 1986). They are also expected to act as analgesics (Hill, Hughes and Pittaway, *Neuropharmacology* 26:289–300, 1987), and as anticonvulsants (MacVicar, Kerrin and Davison, *Brain Research* 406:130–135, 1987).

Reduced levels of CCK-peptides have been found in the brains of schizophrenic patients compared with controls (Roberts, Ferrier, Lee, Crow, Johnstone, Owens, Bacarese-Hamilton, McGregor, O'Shaughnessey, Polak and Bloom. *Brain Research* 288:199–211, 1983). It has been proposed that changes in the activity of CCK neurones projecting to the nucleus accumbens may play a role in schizophrenic processes by influencing dopaminergic function (Totterdell and Smith, *Neuroscience* 19:181–192, 1986). This is consistent with numerous reports that CCK peptides modulate dopaminergic function in the basal ganglia and particularly the nucleus accumbens (Weiss, Tanzer, and Ettenberg, *Pharmacology, Biochemistry and Behaviour* 30:309–317, 1988; Schneider, Allpert and Iversen, *Peptides* 4, 749–753, 1983). It may therefore be expected that agents modifying CCK receptor activity may have therapeutic value in conditions associated with disturbed function of central dopaminergic function such as schizophrenia and Parkinson's disease.

CCK and gastrin peptides share a common carboxy terminal pentapeptide sequence and CCK peptides can bind to the gastrin receptor of the stomach mucosa and elicit acid secretion in many species including human (Konturek, *Gastrointestinal Hormones*, Ch. 23, pp 529–564, 1980, ed. G. B. J. Glass, Raven Press, NY). Antagonists of the CCK-B receptor would also be expected to be antagonists at the stomach gastrin receptor and this would also be of value for conditions involving excessive acid secretion.

CCK and gastrin peptides have trophic effects on the pancreas and various tissues of the gastrointestinal tract (Johnson, ibid., pp 507–527), actions which are associated with increased DNA and RNA synthesis. Moreover, gastrin secreting cells are associated with certain gastrointestinal tumors as in the Zollinger-Ellison syndrome (Stadil, *ibid.*, pp 729–739), and some colorectal tumors may also be gastrin/CCK dependent (Singh, Walker, Townsend and Thompson, *Cancer Research* 46:1612, 1986, and Smith, J. P., *Gastroenterology* 95:1541, 1988). Antagonists of CCK/gastrin receptors could therefore be of therapeutic value as antitumor agents.

The CCK peptides are widely distributed in various organs of the body including the gastrointestinal tract, endocrine glands, and the nerves of the peripheral and central nervous systems. Various biologically active forms have been identified including a 33 amino acid hormone and various carboxyl-terminus fragments of this peptide (e.g., the octapeptide CCK26-33 and the tetrapeptide CCK30-33). (G. J. Dockray, *Br. Med. Bull.* 38(3):253–258, 1982).

The various CCK peptides are thought to be involved in the control of smooth muscle contractility, exocrine and endocrine gland secretion, sensory nerve transmission, and numerous brain functions. Administration of the native peptides cause gall bladder contraction, amylase secretion, excitation of central neurons, inhibition of feeding, anticonvulsive actions and other behavioral effects. ("Cholecystokinin: Isolation, Structure and Functions," G. B. J. Glass, Ed., Raven Press, New York, 1980, pp 169–221; J. E. Morley, *Life Sciences* 27:355–368, 1980; "Cholecystokinin in the Nervous System," J. de Belleroche and G. J. Dockray, Ed., Ellis Horwood, Chichester, England, 1984, pp 110–127.)

The high concentrations of CCK peptides in many brain areas also indicate major brain functions for these peptides (G. J. Dockray, *Br. Med. Bull.* 38(3):253–258, 1982). The most abundant form of brain CCK found is CCK26-33, although small quantities of CCK30-33 exist (Rehfeld and Gotterman, *J. Neurochem.*, 32:1339–1341, 1979). The role of central nervous system CCK is not known with certainty; but it has been implicated in the control of feeding (Della-Fera and Baile, *Science* 206:471–473, 1979).

Currently available appetite suppressant drugs either act peripherally, by increasing energy expenditure (such as thyroxine), or in some other manner (such as the biguanides), or act by exerting a central effect on appetite or satiety.

Centrally acting appetite suppressants either potentiate central catecholamine pathways and tend to be stimulants (for example, amphetamine), or influence serotonergic pathways (for example, fenfluramine). Other forms of drug therapy include bulking agents which act by filling the stomach, thereby inducing a "feeling" of satiety.

CCK is known to be present in some cortical interneurones which also contain gamma-aminobutyric acid (GABA) (H. Demeulemeester et al, *J. Neuroscience* 8:988–1000, 1988). Agents that modify GABA action may have utility as anxiolytic or hypnotic agents (S. C. Harvey, *The Pharmacological Basis of Therapeutics* (7th ed.) 1985, pp 339–371, MacMillan). Thus, agents which modify CCK action may have parallel anxiolytic or hypnotic activities. The role of CCK in anxiety is disclosed in TIPS 11:271-3, 1990.

SUMMARY OF THE INVENTION

The invention relates to novel compounds of the formula

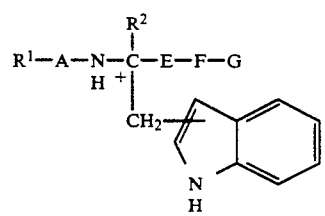

and the pharmaceutically acceptable salts thereof wherein $R^1$, $R^2$, A, E, F, and G are as defined hereinbelow.

In commonly assigned copending applications 07/576,308, 07/576,628, 07/576,296, 07/576,315, 07/576,297, filed on Aug. 31, 1990 by Horwell, et al, the disclosures of which are incorporated herein by reference, CCK antagonists are disclosed.

In the continuation-in-part applications of the above applications also commonly owned and copending 07/726,656, 07/726,655, 07/726,654, 07/726,653, and 07/726,651, filed on even date herewith by Horwell, et al, the disclosures of which are incorporated herein by reference, CCK antagonists are disclosed.

The invention also relates to a pharmaceutical composition containing an effective amount of a compound according to formula I in combination with a pharmaceutically acceptable carrier in unit dosage form effective for appetite suppression.

The compounds are also useful as anxiolytics, antipsychotics, especially for treating schizophrenic behavior, as agents in treating disorders of the extrapyramidal motor system, as agents for blocking the trophic and growth stimulating actions of CCK and gastrin, and as agents for treating gastrointestinal motility.

Compounds of the invention are also useful as analgesics and potentiate the effect of morphine. They can be used as an adjunct to morphine and other opioids in the treatment of severe pain such as cancer pain and reduce the dose of morphine in treatment of pain where morphine is contraindicated.

An additional use for compounds of formula I is that the suitable radiolabelled iodine-131 or iodine-127 isotope gives an agent useful in the treatment of gastrin dependent tumors such as those found in colonic cancers. I-125 radiolabelled compounds of formula I can also be used as a diagnostic agent by localization of gastrin and CCK-B receptors in both peripheral and central tissue.

The invention further relates to a method of appetite suppression in mammals which comprises administering an amount effective to suppress appetite of the composition described above to a mammal in need of such treatment.

The invention also relates to a pharmaceutical composition for reducing gastric acid secretion containing an effective amount of a compound of formula I in combination with a pharmaceutically acceptable carrier in unit dosage form effective for reducing gastric acid secretion.

The invention also relates to a method for reducing gastric acid secretion in mammals which comprises administering an amount effective for gastric acid secretion reduction of the composition described above to a mammal in need of such treatment.

The invention also relates to a pharmaceutical composition containing an effective amount of a compound of formula I in combination with a pharmaceutically acceptable carrier in unit dosage form effective for reducing anxiety.

The invention also relates to a method for reducing anxiety in mammals which comprises administering an amount effective for anxiety reduction of the composition described above to a mammal in need of such treatment.

The invention also relates to a pharmaceutical composition containing an effective amount of a compound of formula I in combination with a pharmaceutically acceptable carrier in unit dosage form effective for treating gastrointestinal ulcers.

The invention further relates to a method for treating gastrointestinal ulcers in mammals which comprises administering an amount effective for gastrointestinal ulcer treatment of the composition as described above to a mammal in need of such treatment.

The invention also relates to a pharmaceutical composition containing an effective amount of a compound of formula I in combination with a pharmaceutically acceptable carrier in unit dosage form effective for treating psychosis, i.e., schizophrenia.

The invention further relates to a method for treating psychosis in mammals which comprises administering an amount effective for treating psychoses of a composition as described above to a mammal in need of such treatment.

The invention also relates to pharmaceutical compositions effective for stimulating or blocking CCK or gastrin receptors, for altering the activity of brain neurons, for schizophrenia, for treating disorders of the extrapyramidal motor system, for blocking the trophic and growth stimulating actions of CCK and gastrin, and for treating gastrointestinal motility.

The invention also relates to a pharmaceutical composition for preventing the withdrawal response produced by chronic treatment or abuse of drugs or alcohol.

The invention further relates to a method for treating the withdrawal response produced by withdrawal from chronic treatment or withdrawal from abuse of drugs or alcohol. Such drugs include benzodiazepines, especially diazepam, cocaine, alcohol, and nicotine. Withdrawal symptoms are treated by administration of an effective withdrawal treating amount of a compound of the instant invention.

The invention also relates to a pharmaceutical composition containing an effective amount of a compound of formula I in combination with a pharmaceutically acceptable carrier in unit dosage form effective for treating and/or preventing panic.

The invention also relates to a method for treating and/or preventing panic in mammals which comprises administering an amount effective for panic treatment and/or prevention of the composition described above to a mammal in need of such treatment.

The invention further relates to the use of the compounds of formula I to prepare pharmaceutical and diagnostic compositions for the treatment and diagnosis of the conditions described above.

The invention further provides processes for the preparation of compounds of formula I.

The invention further provides novel intermediates useful in the preparation of compounds of formula I and also provides processes for the preparation of the intermediates.

DETAILED DESCRIPTION

The compounds of the present invention are formed by the condensation of two modified amino acids and are therefore *not* peptides. Rather they are "peptoids", synthetic peptide-related compounds differing from natural peptides in that the substituent group $R^2$ is not hydrogen.

The compounds of the present invention are represented by the formula

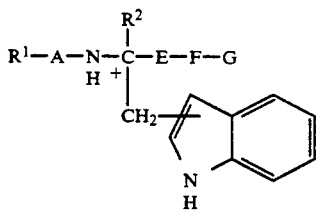

or a pharmaceutically acceptable salt thereof wherein:
$R^1$ is a cyclo- or polycycloalkyl hydrocarbon of from three to twelve carbon atoms with from zero to four substituents, each independently selected from the group consisting of: a straight or branched alkyl of from one to six carbon atoms, halogen, CN, $OR^*$, $SR^*$, $CO_2R^*$, $CF_3$, $NR^5R^6$, or $-(CH_2)_nOR^5$, wherein $R^*$ is hydrogen, straight or branched alkyl of from one to six carbon atoms, $R^5$ and $R^6$ are each independently hydrogen or alkyl of from one to six carbon atoms; and n is an integer from zero to six;

A is $-(CH_2)_nCO-$, $-SO_2-$, $-SO-$, $-NHCO-$,

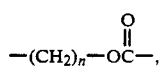

$-SCO-$, $-O-(CH_2)_nCO-$ or $-HC=CH-CO-$ wherein n is an integer from zero to six;

$R^2$ is a straight or branched alkyl of from one to six carbon atoms, $-HC=CH_2$, $-C\equiv CH$, $-CH_2-CH=CH_2$, $-(CH_2)_nC\equiv CH$, $-(CH_2)_nAr$, $-(CH_2)_nOR^*$, $-(CH_2)_nOAr$, $-(CH_2)_nCO_2R^*$, $-(CH_2)_nNR^5R^6$ wherein n, R' $R^5$ and $R^6$ are as defined above and Ar is a mono- or polycyclic unsubstituted or substituted carbo- or heterocyclic aromatic or hydroaromatic moiety;

E is $-CONH-$, $-NHCO-$, $-OCO-$, $-COO-$, $-(CH_2)_mNR^3-$, $-(CH_2)_mO-$, $-(CH_2)_mS-$, $-C\equiv C-$,

$-SO_2NR^3-$, $-NR^3SO_2-$, $-NHCONH-$, $-CH_2CO-$, $-COCH_2-$, $-(CH_2)_mNHCO-$, $-(CH_2)_mCONH-$ wherein m is an integer of from 1-5,

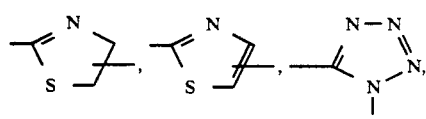

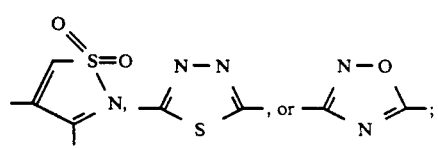

F is a bond, $-CH(R)CO-$ wherein R is $-(CH_2)_mCOOH$, $-(CH_2)_mSCH_3$, $-(CH_2)_nCH(CH_3)CH_3$, $-(CH_2)_nCH_3$, $-(CHR^3)_p-(CHR^4)_q-COOR^*$, $-(CHR^3)_p-(CHR^4)_q-Z$ wherein p and q are each independently 0, 1, or 2 and wherein F is a desamino genetically coded amino acid, excluding Tyr, Phe, Trp, and His;

$R^3$ and $R^4$ are each independently selected from hydrogen, $R^2$ and $-(CH_2)_{n'}-B-D$ wherein:

n' is an integer of from zero to three;

B is a bond,
$-OCO(CH_2)_n-$,
$-O(CH_2)_n-$,
$-NHCO(CH_2)_n-$,
$-CONH(CH_2)_n-$,
$-NHCOCH=CH-$,
$-COO(CH_2)_n-$,
$-CO(CH_2)_n-$,
$-S-(CH_2)_n-$,
$-S(=O)-(CH_2)_n-$,
$-SO_2-(CH_2)_n-$,
$-NHSO_2-(CH_2)_n-$,
$-SO_2NH-(CH_2)_n-$,

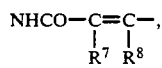

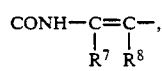

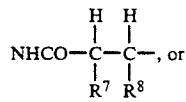

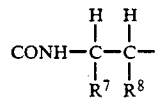

wherein $R^7$ and $R^8$ are independently selected from hydrogen and $R^2$ or together form a ring $(CH_2)_m$ wherein m is an integer of from 1 to 5 and n is as defined above;

D is
$-COOR^*$,
$-CH_2OR^*$,
$-CHR^2OR^*$,
$-CH_2SR^*$,
$-CHR^2SR^*$,
$-CONR^5R^6$,
$-CN$,
$-NR^5R^6$,
$-OH$,
$-H$ or an acid replacement such as tetrazole, or

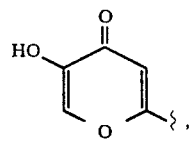

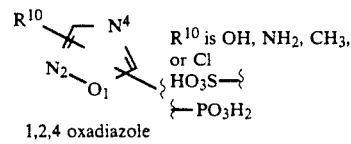

1,2,4 oxadiazole

-continued

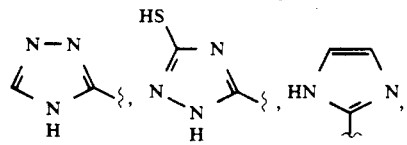

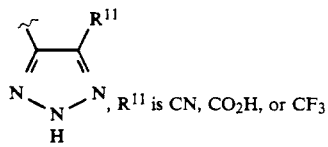, $R^{11}$ is CN, $CO_2H$, or $CF_3$

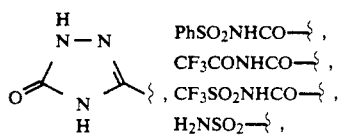   $PhSO_2NHCO-$,
$CF_3CONHCO-$,
$CF_3SO_2NHCO-$,
$H_2NSO_2-$,

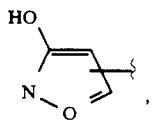,

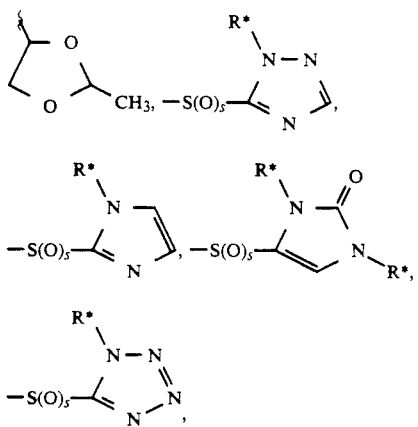

wherein s is an integer of from 0 to 2,
wherein $R^*$, $R^2$, $R^5$, and $R^6$ are as defined above; and
G is $R^3$ as defined above, and
G cannot be hydrogen when F is a bond.

Preferred cycloalkyl or polycycloalkyl substituents have from six to ten carbon atoms.

Preferred compounds of the instant invention are those wherein cycloalkyl is a substituted or unsubstituted

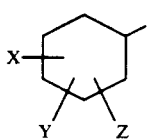, and wherein polycycloalkyl is selected from

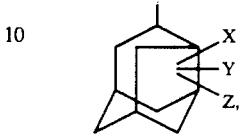

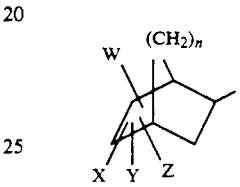

wherein W, X, Y, and Z are each independently hydrogen, a straight or branched alkyl of from one to six carbon atoms, $CF_3$, $NR^5R^6$, $-(CH_2)_nCO_2R^*$, or CN, F, Cl, Br, $OR^*$, $SR^*$, wherein $R^*$ is hydrogen or a straight or branched alkyl of from one to six carbon atoms and $R^5$ and $R^6$ are as defined above and n is an integer of from 1 to 3.

Other preferred compounds of the instant invention are those wherein
$R^1$ is 2-adamantyl or 1-(S)-2-endobornyl;
A is $-NHCO-$, $-OCO-$, $-SO_2-$, $-S(=O)_n-$, $-CH_2CO-$;
$R^2$ is $-CH_3$, $-CH_2CO_2H$, or $-CH_2C\equiv CH$;
E is $-CONH-$;
F is a desamino form of alanine, substituted β-alanine, arginine, asparagine, aspartic acid, cysteine, glutamic acid, glutamine, glycine, isoleucine, leucine, lysine, methionine, serine, threonine, valine, and $CHR^3CHR^4CO_2R^*$, and G is OH, $NH_2$, $-NHCOCH_2CH_2CO_2H$,
$-NHCOCH_2CH_2COCH_2C_6H_5$, $-NHCOCH_2CO_2H$, $-NHCOCH=CHCO_2H$, $-CH_2CO_2H$, $-OCOCH_2CH_2CO_2H$, $-CH_2SCH_2CO_2H$, $CH_2SCH_2CH_2CO_2H$, $-CH_2CO_2H$, $-OCOCH_2CH_2CO_2H$, $-CH_2SCH_2CO_2H$, $-CH_2SCH_2CH_2CO_2H$,

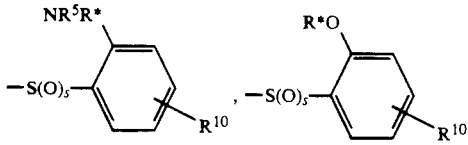

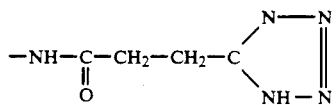

More preferred compounds of the instant invention are those wherein
$R^1$ is 2-adamantyl or 1-(S)-2-endobornyl;
A is $-NHCO-$, $-OCO-$, $-SO_2-$, $-S(=O)-$ or $-CH_2CO-$;

$R^2$ is —$CH_3$, —$CH_2CO_2H$ or —$CH_2C\equiv CH$;

E is CONH; and

F is CH(R)CO— wherein R is —$CH_2CO_2H$, —$CH_2CH_2SCH_3$, —$CH_2CH(CH_3)CH_3$, —$(CH_2)_3CH_3$; and G is OH, —$NH_2$, —$NHCOCH_2CH_2CO_2H$, —$NHCOCH_2CH_2CO_2CH_2Ph$,

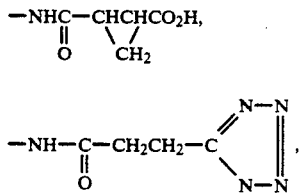

—$CH_2SCH_2CO_2H$, —$CH_2SCH_2CH_2CO_2H$, and —$NHCOCH=CHCO_2H$.

The D and L configurations are possible at the chiral centers and are included in the scope of the invention: Preferred is when $R^2$ is —$CH_3$[D] configuration.

Most preferred compounds of the instant invention are:

(R)-N-[3-(1H-indol-3-yl)-2-methyl-1-oxo-2-[[(tricyclo[3.3.1.1$^{3,7}$]dec-2-yloxy)carbonyl]amino]propyl]glycine, (R)-4-[[3-(1H indol-3-yl)-2-methyl-1-oxo-2-[[(tricyclo[3.3.1.1$^{3,7}$]dec-2-yloxy)carbonyl]amino]propyl]amino]butanoic acid, Methyl (R)-4-[[3-(1H-indol-3-yl)-2-methyl-1-oxo-2-[[(tricyclo[3.3.1.1$^{3,7}$]dec-2-yloxy)carbonyl]amino]propyl]amino]butanoate, Phenylmethyl (R)-3-[[3-(1H-indol-3-yl)-2-methyl-1-oxo-2[[(tricyclo[3.3.1.1$^{3,7}$]dec-2-yloxy)carbonyl]amino] propyl]amino]propanoate, Methyl N-[α-methyl-N-[(tricyclo[3.3.1.1$^{3,7}$]dec-2-yloxy)carbonyl]-D-tryptophyl]-β-alanine, Phenylmethyl N-[2-methyl-N-[(tricyclo[3.3.1.1$^{3,7}$]-dec-2-yloxy)carbonyl]-D-tryptophyl]glycine, N-[α-methyl-N-[(tricyclo[3.3.1.1$^{3,7}$]dec-2-yloxy)carbonyl]-D-tryptophyl]-β-alanine, Tricyclo[3.3.1.1$^{3,7}$]dec-2-yl [1S-[1R*(S*),2R*]]-[2-[[1-(hydroxymethyl)-2-methylbutyl]amino]-1-(1H-indol-3 ylmethyl)-1-methyl-2-oxoethyl]carbamate, Tricyclo[3.3.1.1$^{3,7}$]dec-2-yl [R-(R*,S*)]-[2-[[1-(hydroxymethyl)-3-methylbutyl]amino]-1-(1H-indol-3-ylmethyl)-1-methyl-2-oxoethyl]carbamate, Methyl N-[α-methyl—N [(tricyclo[3.3.1.1$^{3,7}$]dec-2-yloxy)carbonyl]-D-tryptophyl]-L-methionine, N-[α-methyl-N-[(tricyclo[3.3.1.1$^{3,7}$]dec-2-yloxy)carbonyl]-D-tryptophyl]-L-methionine, Methyl N-[N-[α-methyl-N-[(tricyclo[3.3.1.1$^{3,7}$]dec-2-yloxy)carbonyl]-D-tryptophyl]-L-methionyl]-β-alanine, N-[S-methyl-N-[α-methyl-N-[(tricyclo[3.3.1.1$^{3,7}$]dec-2-yloxy)carbonyl]-D-tryptophyl]-D-cysteinyl-β-alanine, S-methyl-N-[α-methyl-N-[(tricyclo[3.3.1.1$^{3,7}$]dec-2-yloxy)carbonyl]-D-tryptophyl]-D-cysteine, N-[α-Methyl-[N-[(tricyclo[3.3.1.1$^{3,7}$] dec-2-yloxy)carbonyl]-D-tryptophyl]-γ- (methylsulfinyl)-L-α-aminobutanoic acid and N-[α-methyl-N-[(tricyclo[3.3.1.1$^{3,7}$]dec-2-yloxy)carbonyl]-D-tryptophyl]-γ-(methylsulfonyl)-L-α-amino-butanoic acid.

The compounds of the present invention include compounds of formula I wherein the indole moiety is a 2- or a 3-indolyl.

The compounds include solvates and hydrates and pharmaceutically acceptable salts of the compounds of formula I.

The compounds of the present invention can have multiple chiral centers including those designated in the above formula I by a †, depending on their structures. In addition, of asymmetry may exist on substituents $R^1$, $R^9$, $R^3$, and $R^4$. In particular the compounds of the present invention may exist as diastereomers, mixtures of diastereomers, or as the mixed or the individual optical enantiomers. The present invention contemplates all such forms of the compounds. The mixtures of diastereomers are typically obtained as a result of the reactions described more fully below. Individual diastereomers may be separated from mixtures of the diastereomers by conventional techniques such as column chromatography or repetitive recrystallizations. Individual enantiomers may be separated by convention method well known in the art such as conversion to a salt with an optically active compound, followed by separation by chromatography or recrystallization and reconversion to the nonsalt form.

The compounds of the present invention can be formed by coupling individual substituted α-amino acids by methods well known in the art. (See, for example, standard synthetic methods discussed in the multi-volume treatise "The Peptides, Analysis, Synthesis, Biology," by Gross and Meienhofer, Academic Press, New York.) The individual substituted alpha amino acid starting materials are generally known or, if not known, may be synthesized and, if desired, resolved by methods within the skill of the art. (Synthesis of racemic [DL]-α-methyl tryptophan methyl ester—see Braña, M. F., et al, J. Heterocyclic Chem. 17:829, 1980.)

A key intermediate in the preparation of compounds of formula I is a compound of formula

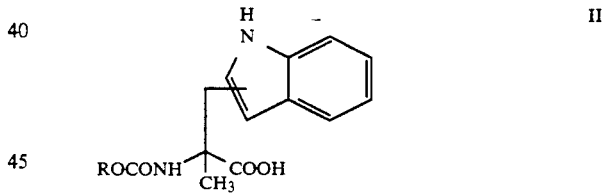

II wherein R is selected from $R^1$, 9-fluorenylmethyl, Bz and other suitable N-blocking groups. These are useful as intermediates in the preparation of compounds of formula I. The compounds wherein R is 1-adamantyl, 2-adamantyl, 4-protoadamantyl, exo-bornyl, endo-bornyl, exo-norbornyl, endo-norbornyl, 2-methylcyclohexyl, 2-chlorocyclohexyl, or camphoryl are novel and are preferred.

The disclosure of U.S. Pat. No. 4,757,151 is hereby incorporated by reference. It describes the 9-fluorenylmethyl blocking group.

Compounds of formula II are prepared by reacting

ROH    III wherein R is as defined above, with phosgene or a phosgene substitute to produce a corresponding compound of formula ROCOCl    IV and then reacting a compound of formula IV with α-methyltryptophan to produce the desired compound of formula II above.

Alternatively, a compound of formula IV can be reacted with, for example, an α-methyltryptophan methyl ester to produce

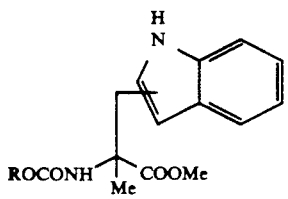

which can be converted to a compound of formula II by known means such as hydrolysis with aqueous lithium hydroxide.

Scheme I below illustrates procedures for preparing intermediates useful in producing final products of formula I.

Key intermediate (2) is prepared from the alcohol form of a radical selected from 1-adamantyl, 2-adamantyl, 4-protoadamantyl, 9-fluorenylmethyl, exobornyl, endo bornyl, exo-norbornyl, endo-norbornyl, 2-methylcyclohexyl, 2-chlorocyclohexyl, and camphoryl. The alcohol is dissolved in a solvent such as methylene chloride. It is then converted to the corresponding chloroformate by reaction with bis(trichloromethyl) carbonate in pyridine at about 0° C. The product is formed by condensation with an amine such as α-methyl-D-tryptophan methyl ester. The reaction is carried out in a solvent such as THF to produce, for example, N-[(2-adamantyloxy)carbonyl]-α-methyl-D-tryptophan methyl ester. This is then treated with lithium hydroxide and stirred at room temperature overnight to produce the corresponding carboxylic acid. This novel key intermediate (2) is useful in the production of compounds of formula I as described hereinafter in Schemes II and III.

Alternatively a chloroformate can be converted to (2) by reaction with an alkaline solution of α-methyl-DL-tryptophan.

SCHEME I
INTERMEDIATES

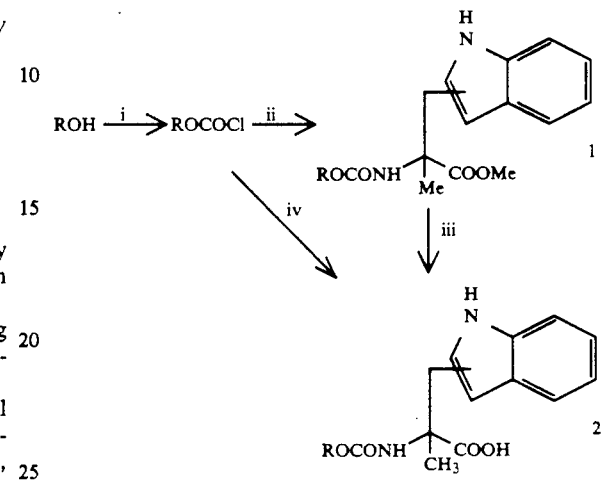

KEY
(i) COCl$_2$, diphosgene or triphosgene, pyridine
(ii) α-methyl tryptophan methylester (for example)
(iii) LiOH, aq. 1,4-dioxan
(iv) α-methyl tryptophan Scheme II shows synthetic steps for making compounds of the instant invention. The key intermediate is 2-Adoc-α-methyltryptophan. When this is treated with N,N'-dicyclohexylcarbodiimide in the presence of pentafluorophenol in ethyl acetate solution. This afforded the active pentafluorophenylester of the 2-Adoc-α-methyltryptophan. This was then further treated with the appropriate amine to afford Examples 1, 3, 5, 7, 8, and 9. The esters were cleaned to the corresponding carboxylic acids either by hydrolysis using LiOH or hydrogenation over Pd/C as appropriate, giving Examples 2, 4, and 6.

SCHEME II

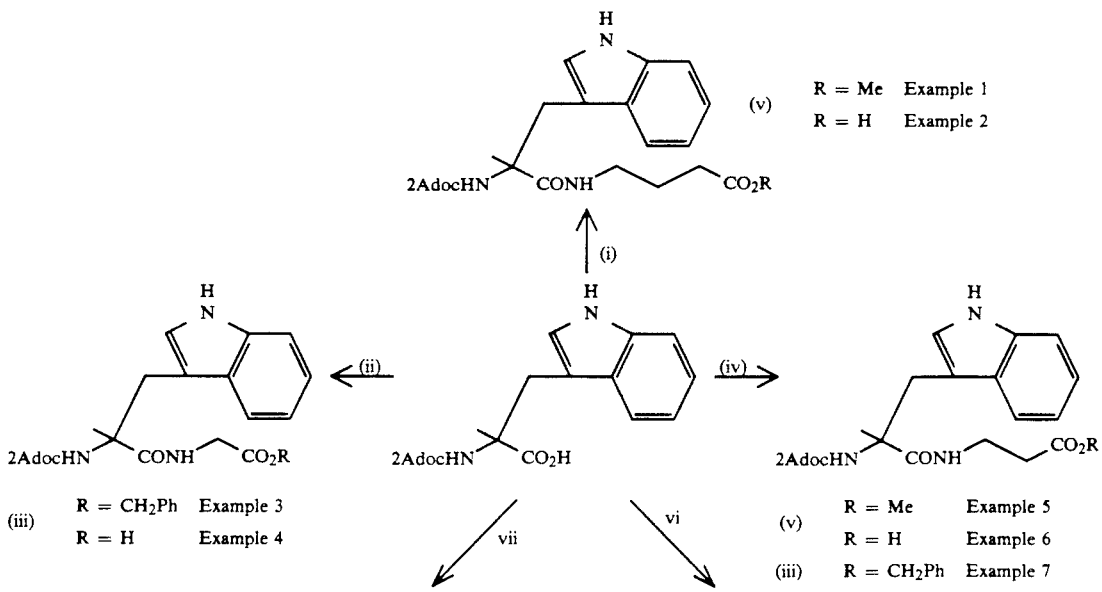

-continued
SCHEME II

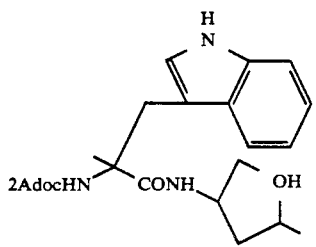

Example 8

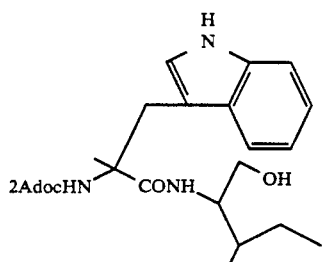

Example 9

(i) DCC, PFP, H₂N~~~CO₂Me (ii) DCC, PFP, H₂N~~~CO₂CH₂Ph (iii) H₂, Pd/C (iv) DCC, PFP H₂N~~~CO₂Me
   or H₂N~~~CO₂CH₂Ph (v) LiOH, H₂O
(vi) DCC, PFP, isoleucinol
(vii) DCC, PFP, leucinol Scheme III outlines the synthesis of Examples 10, 11, and 12. The key intermediate, 2-adoc-α-MeTrpOH, was treated with N,N′-dicyclohexylcarbodiimide and 1-hydroxybenzotriazole in EtOAc. This gave the HoBT active ester which reacted readily with methionine methyl ester to give Example 10. This gave Example 11 upon hydrolysis of the ester with LiOH in aqueous THF. The HoBT active ester of this carboxylic acid was prepared as above and this further reacted with β-alanine methyl ester, affording Example 12.

SCHEME III

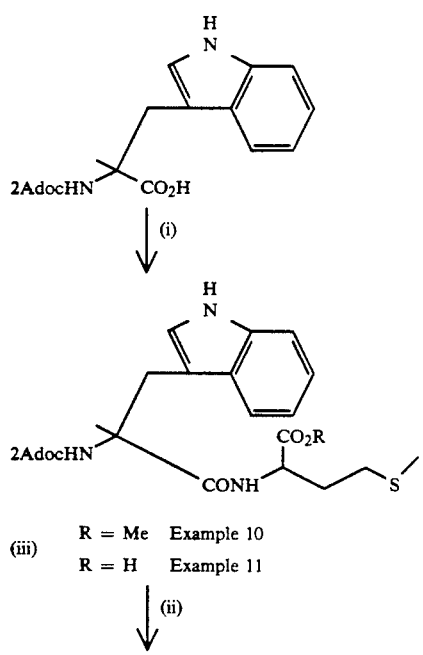

R = Me  Example 10
R = H   Example 11

-continued
SCHEME III

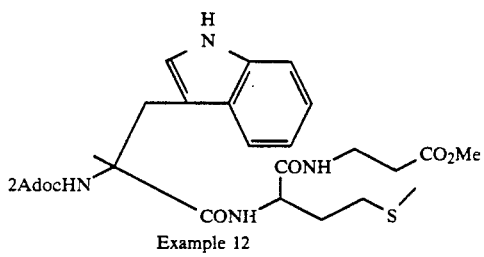

Example 12

(i) DCC, HOBT, Methionine, ETOAc
(ii) DCC, HOBT, β-alanine, ETOAc
(iii) LiOH, H₂O, THF

BIOLOGICAL ACTIVITY

The biological activity of compounds of the present invention was evaluated employing an initial screening test which rapidly and accurately measured the binding of the tested compound to known CCK receptor sites. Specific CCK receptors have been shown to exist in the central nervous system. (See Hays et al, *Neuropeptides* 1:53–62, 1980; and Satuer et al, *Science* 208:1155–1156, 1980.

In this screening test, the cerebral cortices taken from male CFLP mice weighing between 30–40 g were dissected on ice, weighed, and homogenized in 10 volumes of 50 mM Tris-HCl buffer (pH 7.4 at 0°–4° C.). The resulting suspension was centrifuged, the supernate was discarded, and the pellet was washed by resuspension in Tris-HCl buffer followed by recentrifugation. The final pellet was resuspended in 20 volumes of 10 nM Hepes buffer (pH 7.2 at 23° C.) containing 130 mM NaCl, 4.7 nM KCl, 5 nM MgCl₂, 1 nM EDTA, 5 mg/mL bovine albumin, and bacitracin (0.25 mg/mL).

In saturation studies, cerebral cortical membranes were incubated at 23° C. for 120 minutes in a final volume of 500 μL of Hepes incubation buffer (pH 7.2)

together with 0.2–20 nM tritiated-pentagastrin (Amersham International, England).

In the displacement experiments, membranes were incubated with a single concentration (2 nM) of ligand, together with increasing concentrations ($10^{-11}$ to $10^{-14}$M) of competitive test compound. In each case, the nonspecific binding was defined as that persisting in the presence of the unlabeled octapeptide $CCK_{26-33}$ ($10^{-6}$M).

Following incubation, radioactivity bound to membranes was separated from that free in solution by rapid filtration through Whatman GF/B filters and washed three times with 4 mL of ice cold Tris-HCl buffer. Filters from samples incubated with tritiated-pentagastrin were placed in polyethylene vials with 4 mL of scintillation cocktail, and the radioactivity was estimated by liquid scintillation spectrometry (efficiency 47–52%).

The specific binding to CCK receptor sites was defined as the total bound tritiated-pentagastrin minus the amount of tritiated-pentagastrin bound in the presence of $10^{-6}$ octapeptide, $CCK_{26-33}$.

Saturation curves for specific tritiated-pentagastrin binding to mouse cortical membranes were analyzed by the methods of Scatchard (*Ann. New York Acad. Sci.* 51:660–672, 1949, and Hill (*J. Physiol.* 40:IV–III, 1910, to provide estimates for the maximum number of binding sites ($B_{max}$) and the equilibrium dissociation constant ($K_a$).

In displacement experiments, inhibition curves were analyzed by either logit-log plots or the iterative curve fitting computer program ALLFIT (DeLean, Munson and Redbard, 1978) to provide estimates of the $IC_{50}$ and nH (apparent Hill coefficient) values. ($IC_{50}$ values were defined as the concentration of test compound required to produce 50% inhibition of specific binding.)

The inhibition constant ($K_i$) of the test compound was then calculated according to the Cheng-Prusoff equation:

$$K_i = \frac{IC_{50}}{1 + [L]/K_a}$$

where [L] is the concentration of radiolabel and $K_a$ is the equilibrium dissociation constant.

The $K_i$ values for several representative compounds of the present invention are present in Table I.

Compounds of the present invention are useful as appetite suppressants as based on the tests described hereinbelow.

In the Palatable Diet Feeding assay, adult male Hooded Lister rats weighing between 200–400 g were housed individually and trained to eat a palatable diet. This diet consisted of Nestlés sweetened condensed milk, powdered rat food and rat water which when blended together set to a firm consistency. Each rat was presented with 20–30 g of the palatable diet for 30 minutes per day during the light phase of the light-dark cycle over a training period of five days. The intake of palatable diet was measured by weighing the food container before and after the 30-minute access period (limits of accuracy 0.1 g). Care was taken to collect and correct for any spillage of the diet. Rats had free access to pellet food and water except during the 30-minute test period.

After the training period, dose-response curves were constructed for CCK8 and several representative compounds of the present invention (n=8–10 rats per dose level). $MPE_{50}$ values (±95% confidence limits) were obtained for the anorectic effects of these compounds and are shown in Table I.

In therapeutic use as appetite suppression agents, the compounds of the instant invention are administered to the patient at dosage levels of from about 200 to about 2800 mg per day.

Table I below shows the binding data for compounds of the invention.

TABLE I

| Example Number | Binding Affinity CCK B (nM) |
|---|---|
| 1 | 82.1 |
| 2 | N.T. |
| 3 | 50.4 |
| 4 | 1510 |
| 5 | N.T. |
| 6 | 4380 |
| 7 | 299 |
| 8 | 292 |
| 9 | 225 |
| 10 | 41 |
| 11 | 24 |
| 12 | 30 |

Male Hooded Lister rats (175–250 g) are housed individually and fasted overnight (free access to water). They are anesthetized with urethane (1.5 g/kg IP) and the trachea cannulated to aid spontaneous respiration. The stomach is perfused continuously using a modification of the original method of Ghosh & Schild in "Continuous recording of acid secretion in the rat", *Brit. J. Pharmac.* 13:54–61, 1956 as described by Parsons in "Quantitative studies of drug-induced gastric acid secretion". (Ph.D. Thesis, University of London, 1969). The cavity of the stomach is perfused at a rate of 3 mL/min with 5.4% w/v glucose solution through both the esophageal and body cannula. The fluid is propelled by a roller pump (Gilson, Minipuls 2), through heating coils to bring its temperature to 37°±1° C. The perfusion fluid is collected by the fundic collecting funnel and passed to a pH electrode connected to a Jenway pH meter (PHM6). An output is taken from the pH meter to a Rikadenki chart recorder for the on-line recording of the pH of the gastric perfusate.

Pentagastrin is stored as a frozen aliquot and diluted to the required concentrations with sterile 0.9% w/v NaCl. Novel compounds are dissolved in sterile 0.9% w/v NaCl on the day of the experiment. Drugs are administered IV through a cannulated jugular vein as a bolus in a dose volume of 1 mL/kg washed in with 0.15 mL 0.9% w/v NaCl. Basal pH is allowed to stabilize before administration of compounds is begun. Typically 30 minutes elapses between surgery and the first compound administration.

The compounds of the instant invention are also useful as antiulcer agents as discussed hereinbelow.

Aspirin-induced gastric damage is assessed in groups of 10 rats each.

All animals are fasted for 24 hours before and throughout the experiment. Drug or vehicle is given 10 minutes before an oral dose of 1 mL of a 45-mg/mL suspension of aspirin in 0.5% carboxymethylcellulose (CMC).

The animals are sacrificed 5 hours after aspirin administration and the stomachs removed and opened for examination.

Gastric damage is scored as follows:

| Score | |
|---|---|
| 1 | Small hemorrhage |
| 2 | Large hemorrhage |
| 3 | Small ulcer |
| 4 | Large ulcer |
| 5 | Perforated ulcer |

The specific dosages employed, however, may be varied depending upon the patient, the severity of the condition being treated, and the activity of the compound employed. Determination of optimum dosages is within the skill of the art.

The compounds of the instant invention are also useful as anxiolytic agents as described and discussed below.

Anxiolytic activity is assessed in the light/dark exploration test in the mouse (B. J. Jones, et al, *Brit. J. Pharmac.* 93:985-993, 1988).

The apparatus is an open-topped box, 45 cm long, 27 cm wide, and 27 cm high, divided into a small (2/5) area and a large (3/5) area by a partition that extended 20 cm above the walls. There is a 7.5×7.5 cm opening in the partition at floor level. The small compartment is painted black and the large compartment white. The floor of each compartment is marked into 9 cm squares. The white compartment is illuminated by a 100-watt tungsten bulb 17 cm above the box and the black compartment by a similarly placed 60-watt red bulb. The laboratory is illuminated with red light.

All tests are performed between 13 hundred hours, 0 minutes and 18 hundred hours, 0 minutes. Each mouse is tested by placing it in the center of the white area and allowing it to explore the novel environment for 5 minutes. Its behavior is recorded on videotape and the behavioral analysis is performed subsequently from the recording. Five parameters are measured: the latency to entry into the dark compartment, the time spent in each area, the number of transitions between compartments, the number of lines crossed in each compartment, and the number of rears in each compartment.

In this test an increase in the time spent in the light area is a sensitive measure of, that is directly related to, the anxiolytic effects of several standard anxiolytic drugs. Drugs are dissolved in water or saline and administered either subcutaneously, intraperitoneally, or by mouth (PO) via a stomach needle.

The compounds of the instant invention are useful as antipsychotic agents. Compounds are tested for their ability to reduce the effects of intra-accumbens amphetamine in the rat as described hereinafter.

Male Sprague Dawley (CD) Bradford strain rats are used. The rats were housed in groups of five at a temperature of 21°±2° C. on a 12 hour light-dark cycle of lights-on between 07 hours 00 minutes and 20 hours 00 minutes. Rats are fed CRM diet (Labsure) and allowed water ad libitum.

Rats are anesthetized with chloral hydrate (400 mg/kg SC) and placed in a Kopf stereotaxic frame. Chronically indwelling guide cannulae (constructed of stainless steel tubing 0.65 mm diameter held bilaterally in Parspex holders) are implanted using standard stereotaxic techniques to terminate 3.5 mm above the center of the nucleus accumbens (Ant. 9.4, Vert. 0.0, Lat. 1.6) or 5.0 mm above the central nucleus of the amygdala (Ant. 5.8, Vert. −1.8, Lat. ±4.5) (atlas of De Groot, 1959). The guides are kept patent during a 14 day recovery period using stainless steel stylets, 0.3 mm diameter, which extended 0.5 mm beyond the guide tips.

Rats are manually restrained and the stylets removed. Intracerebral injection cannulae, 0.3 mm diameter, are inserted and drugs delivered in a volume of 0.5 µL over 5 seconds (a further 55 seconds was allowed for deposition) from Hamilton syringes attached via polythene tubing to the injection units. Animals are used on a single occasion only.

Behavioral experiments are conducted between 07 hours 30 minutes and 21 hours 30 minutes in a quiet room maintained at 22°±2° C. Rats are taken from the holding room and allowed 1 hour to adapt to the new environment. Locomotor activity is assessed in individual screened Perspex cages (25×15×15 cm (high) (banked in groups of 30) each fitted with one photocell unit along the longer axis 3.5 cm from the side; this position has been found to minimize spurious activity counts due to, for example, preening and head movements when the animal is stationary. Interruptions of the light beam are recorded every 5 minutes. At this time animals are also observed for the presence of any nonspecific change in locomotor activity, e.g., sedation, prostration, stereotyped movements, that could interfere with the recording of locomotor activity.

The abilities of compounds to inhibit the hyperactivity caused by the injection of amphetamine into the nucleus accumbens of the rat are measured.

An increase in locomotor activity follows the bilateral injection of amphetamine (20 µg) into the nucleus accumbens; peak hyperactivity (50 to 60 counts 5 minutes$^{-1}$) occurs 20 to 40 minutes after injection.

Intraperitoneal injection of the rats with a compound in a dosage range of 1 to 100 mg/kg reduces the hyperactivity caused by the intra-accumbens injection of amphetamine. This test is-known to be predictive of antipsychotic activity (Costall, Domeney & Naylor & Tyers, *Brit. J. Pharmac.* 92:881-894).

The compounds of the instant invention prevent and treat the withdrawal response produced when chronic treatment by a drug is stopped or when alcohol abuse is stopped. These compounds are therefore useful as therapeutic agents in the treatment of chronic drug or alcohol abuse as discussed and described below.

The effect of the compounds of the instant invention is illustrated, for example, in the mouse "light/dark box" test.

Five animals are given nicotine, 0.1 mg/kg i.p. b.d. for 14 days. After a 24-hour withdrawal period, a compound typically is given at a range of 1 to 100 mg/kg i.p. b.d. The increased time spent in the light area is a sensitive measure of the effect of the compound as an agent to treat withdrawal effects from nicotine.

The effect of long-term treatment and withdrawal from nicotine using a compound of the invention. Five mice are given nicotine at 0.1 mg/kg i.p. b.d. for 14 days. After a withdrawal period of 24 hours, the compound is given at 10 mg/kg i.p. b.d. The effect of the compound can be seen in the increase of time spent in the light area.

The effect of long-term treatment and withdrawal from diazepam with intervention with a compound of the invention is demonstrated by the following. Five mice are given diazepam, at 10 mg/kg i.p. b.d. for 7 days. Withdrawal is for a 24-hour period; the compound is given at 1.0 mg/kg i.p. b.d. The increased time spent in the light section shows the effect of the compound.

The effect of a compound of the invention on the long-term treatment and withdrawal from diazepam is demonstrated by the following. Five mice were given diazepam at 10 mg/kg i.p. b.d. for 7 days. After a withdrawal period of 24 hours, the compound is given at 10 mg/kg i.p. b.d. The amount of time spent in the light section after the compound is administered demonstrates the effectiveness of the compound.

The effect of a compound of the invention on the long-term treatment and withdrawal from alcohol is demonstrated by the following. Five mice are given alcohol in drinking water 8% w/v for 14 days. After a withdrawal period of 24 hours, the compound is given typically in the range of 1 to 100 mg/kg i.p. b.d. The amount of time spent in the light section after the compound is administered demonstrates the effectiveness of the compound.

The effect of a compound of the invention on long-term treatment and withdrawal from alcohol is demonstrated by the following. Five mice were given alcohol in drinking water, 8% w/v for 14 days. After a withdrawal period of 24 hours, the compound is given typically in the range of 1 to 100 mg/kg i.p. b.d. The increased time spent in the light section shows the effect of the compound on the mice.

The effectiveness in the long-term treatment and withdrawal from cocaine of a compound of the invention. Five mice are given cocaine typically in the range of 1 to 100 mg/kg i.p. b.d. for 14 days. The increased time in the light section illustrates the effectiveness of the compound in the treatment.

The effect of long-term treatment and withdrawal from cocaine with the intervention of a compound of the invention is demonstrated by the following. Five mice are given cocaine typically in the range of 1 to 100 mg/kg i.p. b.d. for 14 days after a withdrawal period of 24 hours, the compound is given typically in the range of 1 to 100 mg/kg i.p. b.d. The effect of intervention with the compound is shown by the increase in time spent in the light section.

The anxiolytic effects of a compound of the invention is shown in the Rat Social Interaction Test typically in the range of 1 to 100 mg/kg when paired rats are dosed s.c. The anxiolytic effect of the compound are indicated by the increase in time spent in social interaction compared with the control value C. (Costall, B., University of Bradford)

The anxiolytic effects of a compound of the invention is shown in the Rat Elevated X-Maze Test on a dose range of 0.01 to 100 mg/kg s.c. The anxiolytic effect is indicated by the time spent in the open arm end section compared with control C.

Compounds of the invention depress the flexor response in a stimulated spinalized decerebrated rat preparation similar to morphine. The effect of giving a compound with morphine greatly potentiates the effect which lasts for 3 hours.

For preparing pharmaceutical compositions from the compounds of this invention, inert, pharmaceutically acceptable carriers can be either solid or liquid. Solid form preparations include powders, tablets, dispersible granules, capsules, cachets, and suppositories.

A solid carrier can be one or more substances which may also act as diluents, flavoring agents, solubilizers, lubricants, suspending agents, binders, or tablet disintegrating agents; it can also be an encapsulating material.

In powders, the carrier is a finely divided solid which is in a mixture with the finely divided active component. In tablets, the active component is mixed with the carrier having the necessary binding properties in suitable proportions and compacted in the shape and size desired.

For preparing suppository preparations, a low-melting wax such as a mixture of fatty acid glycerides and cocoa butter is first melted and the active ingredient is dispersed therein by, for example, stirring. The molten homogeneous mixture is then poured into convenient sized molds and allowed to cool and solidify.

The powders and tablets preferably contain 5 to about 70% of the active component. Suitable carriers are magnesium carbonate, magnesium stearate, talc, lactose, sugar, pectin, dextrin, starch, tragacanth, methyl cellulose, sodium carboxymethyl cellulose, a low-melting wax, cocoa butter, and the like.

Pharmaceutically acceptable counterions are shown below:

Acetate, benzenesulfonate, benzoate, bicarbonate, bitartrate, bromide, calcium acetate, camsylate, carbonate, chloride, citrate, dihydrochloride, edetate, edisylate, estolate, esylate, fumarate, glucaptate, gluconate, glutamate, glycollylarsanilate, hexylresorcinate, hydrabamine, hydrobromide, hydrochloride, hydrochloride, hydroxynaphthoate, iodide, isethionate, lactate, lactobionate, malate, maleate, mandelate mesylate, methylbromide, methylnitrate, methylsulfate, mucate, napsylate, nitrate, pamoata (embonate), pantothenate, phosphate/ diphosphate, polygalacturonate, salicylate, stearate, subacetate, succinate, sulfate, tannata, tartrate, teoclate, triethiodide, benzathine, chloroprocaine, choline, diethanolamine, ethylenediamine, meglumine, procaine, aluminum, calcium, lithium, magnesium, potassium, sodium, and zinc.

A preferred pharmaceutically acceptable salt is the N-methyl glucamine salt or sodium salt.

The term "preparation" is intended to include the formulation of the active component with encapsulating material as a carrier providing a capsule in which the active component (with or without other carriers) is surrounded by a carrier which is thus in association with it. Similarly, cachets are included.

Tablets, powders, cachets, and capsules can be used as solid dosage forms suitable for oral administration.

Liquid form preparations include solutions, suspensions, and emulsions. Sterile water or water-propylene glycol solutions of the active compounds may be mentioned as an example of liquid preparations suitable for parenteral administration. Liquid preparations can also be formulated in solution in aqueous polyethylene glycol solution.

Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

Preferably the pharmaceutical preparation is in unit dosage form. In such form, the preparation is divided into unit doses containing appropriate quantities of the active component. The unit dosage form can be a packaged preparation, the package containing discrete quantities of the preparation, for example, packeted tablets, capsules, and powders in vials or ampoules. The unit dosage form can also be a capsule, cachet, or tablet itself, or it can be the appropriate number of any of these packaged forms.

The following examples are illustrative of the instant invention. They are not intended to limit the scope.

EXAMPLES

Example 1

Butanoic acid, 4-[[3-(1H-indol-3-yl)-2-methyl-1-oxo-2-[[(tricyclo[3.3.1.1³,⁷]dec-2-yloxy)carbonyl]amino]propyl]amino]-, methyl ester (R)-

(2-Adoc-α-Me-R-TrpNH⌒⌒CO₂Me)

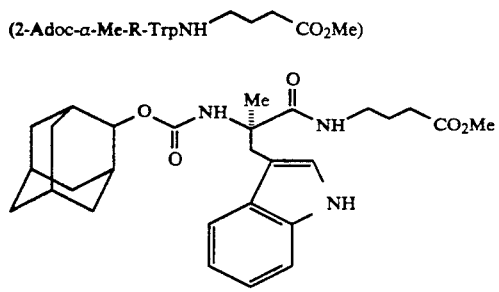

A solution of 2-Adoc-α-Me-R-TrpOH (3.0 g, 7.6 mmol) in EtOAc (40 mL) was treated with pentafluorophenol (1.39 g, 7.60 mmol) and cooled to 0° C. A solution of N,N'-dicyclohexylcarbodiimide (1.56 g, 7.60 mmol) in EtOAc (10 mL) was then added dropwise and the mixture stirred 18 hours at 4° C. The reaction mixture was then filtered and gamma amino butyric acid methyl ester hydrochloride (1.38 g, 9.00 mmol) was added to the filtrate, followed by a dropwise addition of a solution of triethylamine (0.91 g, 9.0 mmol) in EtOAc (10 mL). This mixture was allowed to stir at room temperature for 24 hours, washed with 1M citric acid (2×50 mL), 1M NaHCO₃ solution (2×50 mL) and H₂O (2×50 mL). The organic phase was dried over MgSO₄ and the solvent evaporated in vacuo and the residue chromatographed over reverse phase silica using 25% H₂O in MeOH as eluant to give the product as a noncrystalline solid (3.28 g, 87%); m.p. 65°–70° C. (CH₂Cl₂); [α]20D+27° (C=1, MeOH); IR (film) 3500–3200, 2908, 2855, 1718, 1703, and 1655 cm⁻¹; NMR (CDCl₃) δ 1.48–1.55 (2H, m), 1.58 (3H, s), 1.65–1.85 (10H, m), 1.90 (4H, m), 2.21 (2H, t, J 7Hz), 3.20 (2H, q, J 7Hz), 3.289 (1H, d, J 3.45 (1H, d, J 14 5H), 3.62 (3H, s), 4.83 (1H, s), 5.34 (1H, s), 6.50–6.60 (1H, br m), 6.97 (1H, d, J 2Hz), 7.07 (1H, t, J 7Hz), 7.15 (1H, t, J 7Hz), 7.33 (1H, d, J 8Hz), 7.57 (1H, d, J 8Hz), 8.72 (1H, s); Anal. C₂₈H₃₇N₃O₅; C, H, N.

Example 2

Butanoic acid, 4[3-(1H-indol-3-yl)-2-methyl-1-oxo-2-[[(tricyclo[3.3.1.1³,⁷]dec-2-yloxy)carbonyl]amino]propyl]amino]-, (R)-

(2-Adoc-α-Me-R-TrpNH⌒⌒CO₂H)

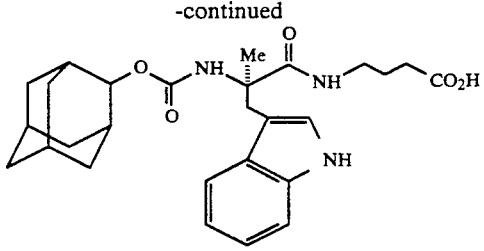

A solution of the methyl ester (Example 1) (2.6 g, 5.2 mmol) in 1,4-dioxan (500 mL) was treated dropwise with a solution of LiOH (104 mL of a 0.05M solution, 5.20 mmol) over 24 hours with vigorous stirring. This mixture was stirred at room temperature for 24 hours and quenched with 1M HCl (5.2 mL). The solvent was removed in vacuo and the residue chromatographed using 0.5% AcOH, 5% MeOH in CH₂Cl₂ to give 80 mg of starting ester along with 1.32 g of product, 55% yield, 77% conversion; m.p. 92 96° C. (CH₂Cl₂); [α]20D+29.3° (c=1, MeOH); IR (film) 3600–3200, 2909, 2856, 1702 and 1651 cm⁻¹; NMR (CDCl₃) δ 1.50–1.55 (2H, m), 1.61 (3H, s), 1.62–2.00 (14H, m), 2.10–2.25 (2H, m), 3.20–3.40 (2H, m), 3.24 (1H, d, J 14.5H), 3.45 (1H, d, J 14.5Hz), 4.84 (1H, ?), 5.47 (1H, s), 6.58–6.65 (1H, brm), 7.03 (1H, d, J 2Hz), 7.09 (1H, t, J 7Hz), 7.17 (1H, t, J 7Hz), 7.35 (1H, d, J 8Hz), 7.57 (1H, d, J 8Hz), 8.59 (1H, s). Anal. C₂₇H₃₅N₃O₅0.2H₂O; C, H, N.

Example 3

Glycine, N-2-methyl-N-[(tricyclo[3.3.1.1³,⁷]dec-2-yloxy)carbonyl]-D-tryptophyl]-, phenylmethyl ester (2-Adoc-α-Me-R-TrpNHCH₂CO₂CH₂Ph)

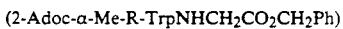

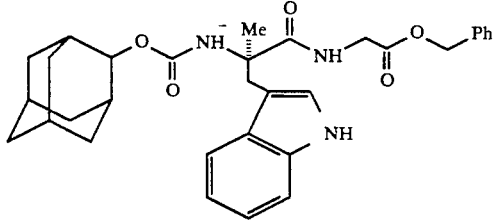

A solution of 2-Adoc-α-Me-R-TrpOH (3.0 g, 7.6 mmol) in EtOAc (40 mL) was treated with pentafluorophenol (1.39 g, 7.6 mmol) in EtoAc (10 mL) was then added dropwise and stirred 12 hours at 4° C. and filtered. Glycine benzyl ester hydrochloride (1.8 g, 9.0 mmol) was added followed by the dropwise addition of triethylamine (0.9 g, 9.0 mmol) in EtOAc (10 mL). This was allowed to stir 18 hours at room temperature. The reaction mixture was then washed with 1M citric acid solution (2×50 mL), 1M NaHCO₃ solution (2×50 mL) and H₂O (2×50 mL). The organic phase was dried over MgSO₄ and evaporated to dryness in vacuo. The residue was chromatographed over reverse phase silica using 25% H₂O in MeOH as eluant to give the product as a white foam (2.83 g, 68%) along with 0.9 g starting active ester, m.p. 76°–82° C. (foam); [α]20D+36° (c-1, MeOH); IR (film) 3500–3200, 908, 2855, 1745, 1702, and 1665 cm⁻¹; NMR (CDCl₃) δ 1.45–1.6 (4H, m), 1.69–2.00 (13H, m), 3.30 (1H, d, J 14.5Hz), 3.50 (1H, d, J 14.5Hz), 3.95–4.10 (2H, m), 4.84 (1H, s), 5.13 (2H, s), 5.21 (1H, s), 6.79 (1H, s), 7.01 (1H, d, J 2Hz), 7.08 (1H, t, J 7Hz), 7.15 (1H, t, J 7Hz), 7.30–7.40 (6H, m), 7.57 (1H, d, J 8Hz), 8.26 (1H, s); MS (FAB) 544.4 (11), 414.3 (11), 348.2 (36), 135.2 (?). Anal. $C_{32}H_{37}N_3O_5$; C, H, N.

Example 4

Glycine, N-[3-(1H-indol-3-yl)-2-methyl-1-oxo-2-[[(tricyclo[3.3.1.1$^{3,7}$]dec-2-yloxy)carbonyl]amino]-propyl-, (R)-

(2-Adoc-α-Me-R-TrpNH⁀CO₂H)

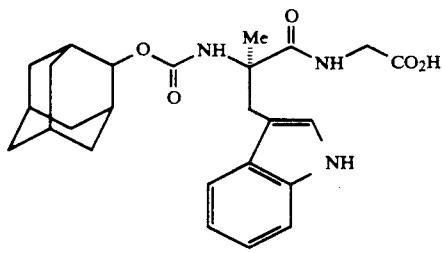

A solution of the benzyl ester (Example 3) (2.5 g, 4.6 mmol) in absolute EtOH (100 mL) was treated with 10% Pd/C (250 mg, 10% w/w) and put under an atmosphere of hydrogen at 50 psi and 20° C. for 5 hours with agitation. The reaction mixture was filtered through a filter aid and the filtrate concentrated in vacuo. The residue was then chromatographed over silica gel using 0.5% AcOH, 5% MeOH in CH₂Cl₂ as eluant to give the product (187.3 g, 90%) as a white solid; m.p. 112°–117° C. (MeOH/H₂O); [α]20D+40° (c=1, MeOH); IR (film) 3500–3200, 2910, 2856, 1702, 1660, and 735 cm⁻¹; NMR (CDCl₃) δ 1.26 (1H, s), 1.51 (1H, s), 1.58 (3H, s), 1.70–2.00 (12H, m), 3.00–4.00 (1H, br), 3.28 (1H, d, J 14.5Hz), 3.45 (1H, d, J 14.5Hz), 3.94 (2H, d, J 5Hz, 4.85 (1H, s), 5.35–5.50 (1H, brs), 6.85 (1H, brt), 7.04 (1H, d, J 2Hz), 7.05–7.18 (2H, m), 7.32 (1H, d, J 8Hz), 7.56 (1H, d, J 8Hz), 8.39 (1H, s); Anal. $C_{25}H_{31}N_3O_5$; C, H, N.

Example 5

2-Adoc-α-Methyl-R-Trp-β-Ala.OMe

A solution of 2-adamantyloxycarbonyl-α-methyl-R-tryptophan (8.0 g, 20 mmol) in EtOAc (100 mL) was treated with pentafluorophenol (3.68 g, 20.0 mmol) and cooled to 0° C. Dicyclohexyl carbodiimide (4.33g, 21.0 mmol) was then added and the mixture left to stir for 18 hours at 0° C. After this time the mixture was filtered and β-alanine methyl ester (2.47 g, 24.0 mmol) added and the mixture left stirring a further 18 hours at room temperature, filtered, and the filtrate washed with 1M HCl (3×30 mL), H₂O (2×30 mL), saturated NaHCO₃ solution (3×30 mL), and H₂O (2×30 mL). The organic phase was dried over MgSO₄ and concentrated in vacuo and the product crystallized from ether to give the ester (7.8 g, 81%); IR (film) 3700–3200, 3000–2800, 7723, 1695, and 1659 cm⁻¹.

Example 6

β-Alanine, N-[α-methyl-N [(tricyclo[3.3.1.1$^{3,7}$]dec-2yloxy)carbonyl]-D-tryptophyl]-

(2-Adoc-α-Me-R-Trp-β-AlaOH)

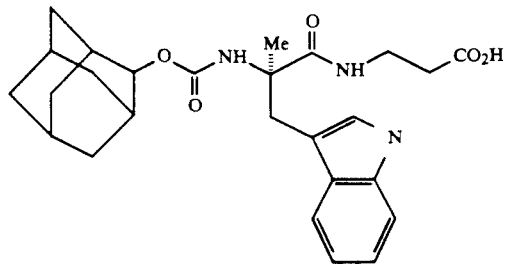

The ester Example 5 (5.20 g, 10.8 mmol) as a solution in 1,4-dioxan (300 mL) was treated with a solution of LiOH.H₂O (454 mg, 10.8 mmol) in H₂O (100 mL) dropwise at room temperature and left stirring 18 hours. 1M HCl (10.8 mL) was added and the mixture distilled to dryness in vacuo and the residue chromatographed over reverse phase silica gel using 70% MeOH in H₂O as eluant to give the product (323 g, 51%) along with starting ester (1 g); m.p. 98°–103° C. (MeOH) [α]20D+29° (c=1, MeOH); IR (film) 3351, 2911, 2855, 1706, and 1658 cm⁻¹; NMR (CDCl₃) δ 1.50–2.00 (17H, m), 2.39 (2H, brs), 3.26 (1H, d, J 15Hz), 3.40–3.50 (3H, m), 4.80 (1H, s), 5.42 (1H, brs), 6.7? (1H, 5, J 6Hz), 6.99 (1H, d, J 2Hz), 7.05–7.20 (2H, ), 7.33 (1H, d, J 8Hz), 7.57 (1H, d, J 8Hz), 8.37 (1H, s); MS m/e (FAB) 468 (M+1) and 217 (100); Anal. $C_{26}H_{33}N_3O_5 \cdot 0.25H_2O$; C, H, N.

Example 7

Propanoic acid, 3-[[3-(1H-indol-3-yl)-2-methyl-1 oxo-2-[[(tricyclo[3.3.1.1$^{3,7}$]dec-2-yloxy)carbonyl-]amino]propyl]amino]-, phenylmethyl ester, (R)-

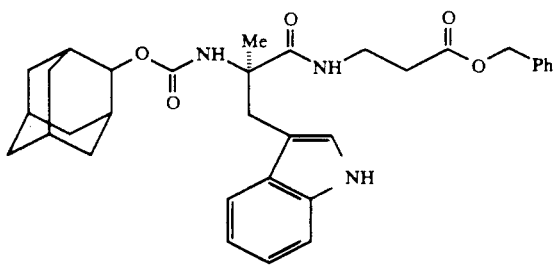

Method exactly as for Example 5 except using glycine benzyl ester, yield 89%; m.p. 204.2° C. (MeOH); IR (film) 3500–3200, 2907, 2855, 1718, 1658 cm³¹ ¹; NMR (CDCl₃) δ 1.52 (3H, s), 1.50–1.60 (2H, m), 1.70–1.85 (8H, m), 1.90–2.05 (4H, m), 2.40–2.55 (2H, m), 3.29 (1H, d, J 14.5Hz), 3.43 (1H, d, J 14.5Hz), 3.46 (2H, q, J) 4.83 (1H, s), 5.00 (2H, s), 5.19 (1H, brs), 6.65–6.75 (1H, brs), 6.96 (1H, d, J 2Hz), 7.09 (1H, dt, J 7 and 1Hz), 7.17 (1H, dt, J 7 and 1Hz), 7.27–7.29 (6H, m), 7.58 (1H, d, J 8Hz), 8.06 (1H, s); Anal. $C_{33}H_{39}N_3O_5$; C, H, N.

Example 8

Carbamic acid,
[2-[[1-(hydroxymethyl)-3-methylbutyl]amino]-1-(1H-indol-3-ylmethyl)-1-methyl-2-oxoethyl]-,
tricyclo[3.3.1.1$^{3,7}$]dec-2-yl ester, [R-(R*,S*)]-

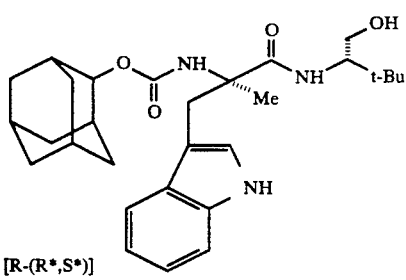

[R-(R*,S*)]

Method as for Example 5, except using (S)(+)isoleucinol, yield 60%; m.p. 99 99.5° C.; IR (film) 3500–3200 2907, 2854, 1700–1620 br cm$^{-1}$; NMR (CDCl$_3$) δ 0.85–0.90 (6H, m), 1.25–1.32 (2H, m), 1.50 (3H, s), 1.51–1.60 (3H, m), 1.65–2.00 (12H, m), 3.10 (1H, br), 3.36 (1H, d, J 14.5Hz), 3.32–3.39 (1H, m), 3.50 (1H, d, J 14.5Hz), 3.72 (1H, dd, J 11.5 and 3Hz), 4.00–4.10 (1H, m), 4.80–4.85 (1H, m), 5.10 (1H, s), 6.12 (1H, d, J 8Hz), 7.00 (1H, d, J 2Hz), 7.09 (1H, t, J 7.5Hz), 7.17 91H, dt, J 7.5 and 1Hz), 7.36 (1H, d, J 8Hz), 7.59 (1H, d, J 8Hz), 8.40 (1H, s).

Example 9

Carbamic acid,
[2-[1-(hydroxymethyl)-2-methylbutyl]amino]-1-(1H indol-3-ylmethyl)-1-methyl-2-oxoethyl]-,
tricyclo[3.3.1.1$^{3,7}$]dec-2-yl ester, [1S-[1R*(S*),2R*]]-

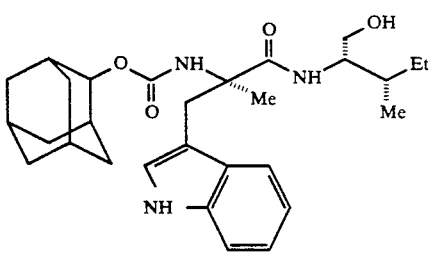

Method as for Example 5 except using (S)(+)isoleucinol, yield 76%; m.p. 79°–82° C.; IR (film) 3500–3200, 2929, 2856, 1697, and 1657 cm$^{-1}$; NMR (CDCl$_3$) δ 0.82–0.88 (6H, m), 1.00–1.20 (2H, m), 1.35–1.45 (1H, m), 1.52 (3H, s), 1.50–1.58 (2H, m), 1.65–2.00 (12H, m), 3.36 (1H, d, J 14.5Hz), 3.45–3.55 (2H, m), 4.20–4.40 (2H, m), 4.83 (1H, s), 5.17 (1H, s), 6.29 (1H, d, J 8.5Hz), 7.01 (1H, d, J 2Hz), 7.09 (1H, t, J 7Hz), 7.17 (1H, t, J 7Hz), 7.36 (1H, d, J 8Hz), 7.59 (1H, d, J 8Hz), 8.61 (1H, s); Anal. C$_{29}$H$_{41}$N$_3$O$_4$.0.4H$_2$O; C, H, N.

Example 10

Methyl
N-[α-methyl-N-[(tricyclo3.3.1.1$^{3,7}$]dec-2-yloxy)carbonyl]-D-tryptophyl]-β-methionine

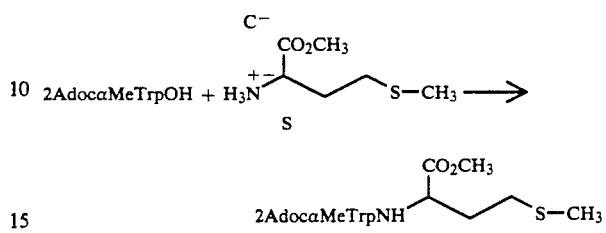

Step 1

N,N'-dicyclohexylcarbodiimide (0.286 g, 1.39 mmol) was added to a stirred solution of 1 hydroxybenzotriazole monohydrate (0.232 g, 1.51 mmol) and the acid (0.500 g, 1.26 mmol) in EtOAc (50 mL) at room temperature. After 1 hour, s methionine hydrochloride (0.377 g, 1.89 mmol) was added followed by triethylamine (0.263 mL, 1.89 mmol) and the mixture stirred for 24 hours at room temperature. The N,N'-dicyclohexylurea was filtered off and the EtOAc washed with aqueous 5% citric acid solution (2×25 mL), saturated NaHCO$_3$ solution (2×25 mL), 25% citric acid (25 mL), and brine (25 mL). The EtOAc was dried over MgSO$_4$, filtered, and the solvent removed in vacuo. The residue was purified by chromatography over silica using 33% EtOAc/67% hexane, then 50% EtOAc/50% n-hexane as eluants, giving the product (0.489 g, 72%) as a white solid, m.p. 6°5–72° C., [α]21D+31.7° (c=0.34, CH); IR (film) 3351, 1743, 1702, and 1665 cm$^{-1}$; NMR (CDCl$_3$) 1.51–2.13 (22H, m), 2.34–2.40 (2H, m), 3.30 (1H, d, J 14.7Hz), 3.49 (1H, d, J 14.8Hz), 3.69 (3H, s), 4.58–4.65 (1H, m), 4.82 (1H, s), 5.24 (1H, bs), 6.94 (1H, d, J 7.2Hz), 7.06–7.20 (3H, m), 7.36 (1H, d, J 8.0Hz), 7.59 (1H, d, J 7.9Hz), 8.19 (1H, s).

Example 11

N-[α-methyl-N-(tricyclo3.3.1.1$^{3,7}$]dec-2-yloxy)carbonyl]-D-tryptophyl]-L methionine

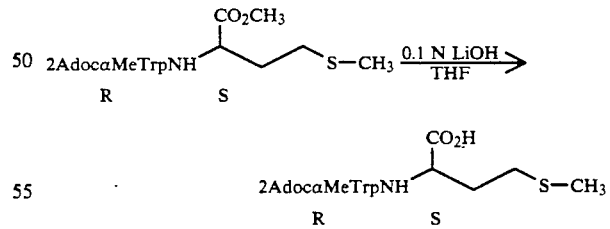

Step 2

To a stirred solution of the methylester (0.423 g, 0.78 mmol) in THF (40 mL) at 0° C. was added dropwise aqueous 0.1N LiOH solution (8.6 mL, 0.86 mmol) over 25 minutes. The cold solution was stirred for 2 hours and then for 18 hours at room temperature. The solvent was removed in vacuo and the residue diluted with water (10 mL) and extracted once with Et$_2$O (25 mL). The aqueous solution was made pH 2 with 0.1N HCl solution and extracted with EtOAc (2×25 mL). The combined EtOAc extracts were washed once with brine (25 mL), dried over MgSO₄, filtered, and the solvents removed in vacuo, giving the product as a white solid (0.351 g, 85%); m.p. 95°-102° C.; $[\alpha]20D+23.9°$ (c=0.9, CDCl₃); IR (film) 3352, 1713, and 1660 cm$^{-1}$; NMR (CDCl₃) 1.52-1.60 (5H, m), 1.71-2.17 (17H, m), 2.45 (3H, t, J 7.2Hz), 3.32 (1H, d, J 14.6Hz), 3.45 (1H, d, J 14.6Hz), 4.59-4.66 (1H, m), 4.84 (1H, s), 5.36 (1H, bs), 7.02 (1H, d, J 2.3Hz), 7.08-7.19 (3H, m), 7.33 (1H, d, J 7.7Hz), 7.57 (1H, d, J 7.7Hz), 8.40 (1H, s).

Example 12

Methyl N-[N-[α-methyl-N-(tricyclo[3.3.1.1$^{3,7}$]dec-2-yloxy)carbonyl]-D-tryptophyl]-L-methionyl]-β-alanine

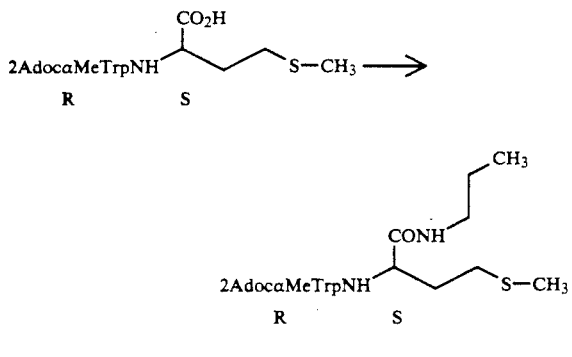

Step 3

To a stirred solution of 1-hydroxybenzotriazole monohydrate (0.082 g, 0.54 mmol) and the acid (0.225 g, 0.43 mmol) in EtOAc (25 mL) was added N,N'-dicyclohexylcarbodiimide (0.048 g, 0.47 mmol) and the mixture stirred for 1 hour at room temperature. This was followed by β-alanine methylester hydrochloride (0.098 g, 0.71 mmol) and triethylamine (0.099 mL, 0.71 mmol) and the mixture stirred at room temperature for 48 hours. The N,N'-dicyclohexylurea was filtered off and the EtOAc washed with aqueous 5% citric acid solution (2×25 mL), saturated NaHCO₃ (2×25 mL), 5% citric acid (25 mL), and brine (25 mL). The EtOAc was dried over MgSO₄, filtered, and the solvent removed in vacuo. The residue was purified by chromatography over silica using 50% n-hexane/50% EtOAc, then 33% n-hexane/67% EtOAc as eluant, giving the product as a white solid (0.168 g, 64%); m.p. 79°-86° C.; $[\alpha]20D+17.7°$ (c=0.20, CHCl₃); IR (film) 3325, 1737, 1694, and 1657 cm$^{-1}$; NMR (CDCl₃) 1.49 (3H, s), 1.34-2.04 (19H, m), 2.26-2.41 (2H, m), 2.53-2.60 (2H, m), 3.42-3.56 (4H, m), 3.67 (3H, s), 4.40-4.59 (1H, m), 4.81, 4.87 (1H, 2s), 5.08, 5.27 (1H, 2s), 6.99 (1H, d, J 2.3Hz), 7.08-7.38 (5H, m), 7.59 (1H, d, J 7.9Hz), 8.23 (1H, 2s).

Example 13

N-[S-methyl N-[α-methyl-N-[(tricyclo[3.3.1.1$^{3,7}$]dec-2-yloxy)carbonyl]-D-tryptophyl]-D-cysteinyl-β-alanine

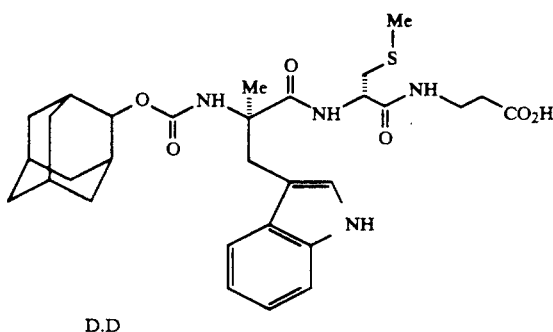

D.D

Step 1

Methyl N-[2-methyl-[(tricyclo[3.3.1.1$^{3,7}$]dec-2-yloxy)carbonyl]-D-tryptophyl-L-methionine

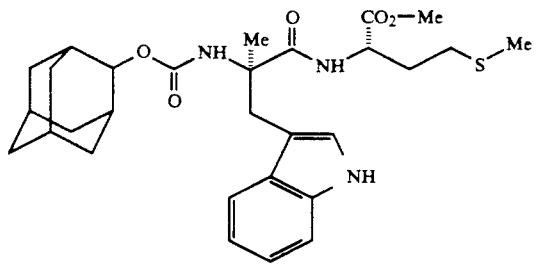

N,N'-dicyclohexylcarbodiimide (0.286 g, 1.39 mmol) was added to a stirred solution of 1 hydroxybenzotriazole monohydrate (0.232 g, 1.51 mmol) and the acid (0.500 g, 1.26 mmol) in EtOAc (50 mL) at room temperature. After 1 hour s-methionine hydrochloride (0.377 g, 1.89 mmol) was added followed by triethylamine (0.263 mL, 1.89 mmol) and the mixture stirred for 24 hours at room temperature. The N,N'-dicyclohexylurea was filtered off and the EtOAc washed with aqueous 5% citric acid solution (2×25 mL), saturated NaHCO₃ solution (2×25 mL), 25% citric acid (25 mL), and brine (25 mL). The EtOAc was dried over MgSO₄, filtered, and the solvent removed in vacuo. The residue was purified by chromatography over silica using 33% EtOAc/67% hexane, then 50% EtOAc/50% n-hexane as eluants, giving the product (0.489 g, 72%) as a white solid, m.p 65°-72° C., $[\alpha]_D^{20}+31.2°$ (c=0.34, CHCl₃); IR (film) 3351, 1743, 1702, and 1665 cm$^{-1}$; NMR (CDCl₃) 1.51-2.13 (22H, m), 2.34-2.40 (2H, m), 3.30 (1H, d, J 14.7Hz), 3.49 (1H, d, J 14.8Hz), 3.69 (3H, s), 4.58-4.65 (1H, m), 4.82 (1H, s), 5.24 (1H, bs), 6.94 (1H, d, J 7.2Hz), 7.06-7.20 (3H, m), 7.36 (1H, d, J 8.0Hz), 7.59 (1H, d, J 7.9Hz), 8.19 (1H, s); Anal. (C₂₉H₃₉N₃O₅S) C, H, N, S.

Step 2

N-[α-methyl-N-[(tricyclo[3.3.1.1³,⁷]dec-2-yloxy)carbonyl-D-tryptophyl]-L-methionine

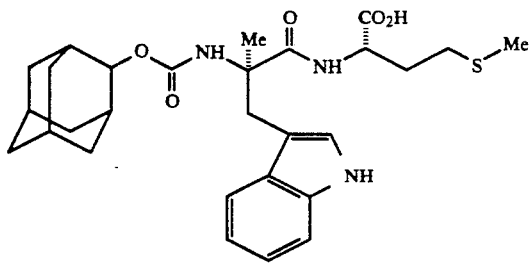

D.I.

To a stirred solution of the methyl ester 0.423 g, 0.78 mmol) in THF (40 mL) at 0° C. was added dropwise aqueous 0.1N LiOH solution (8.6 mL, 0.86 mmol) over 25 minutes. The cold solution was stirred for 2 hours and then for 18 hours at room temperature. The solvent was removed in vacuo and the residue diluted with water (10 mL) and extracted once with Et₂O (25 mL). The aqueous solution was made pH 2 with 0.1N HCl solution and extracted with EtOAc (2×25 mL). The combined EtOAc extracts were washed once with brine (25 mL), dried over MgSO₄, filtered, and the solvents removed in vacuo, giving the product as a white solid (0.351 g, 85%), m.p. 95°-102° C.; $[\alpha]_D^{20}$ +23.9° (c=0.9, CHCl₃); IR (film) 3352, 1713, and 1660 cm⁻¹; NMR (CDCl₃) 1.52-1.60 (5H, m), 1.71-2.17 (17H, m), 2.45 (3H, t, J 7.2Hz), 3.32 (1H, d, J 14.6Hz), 3.45 (1H, d, J 14.6Hz), 4.59-4.66 (1H, m), 4.84 (1H, s), 5.36 (1H, bs), 7.02 (1H, d, J 2.3Hz), 7.08-7.19 (3H, m), 7.33 (1H, d, J 7.7Hz), 7.57 (1H, d, J 7.7Hz), 8.40 (1H, s); Anal. (C₂₈H₃₇N₃O₅S), C, H, N, S.

Step 3

Methyl N-[N-[α-methyl-N-[(tricyclo[3.3.1.1³,⁷]dec-2-yloxy)carbonyl]-D-tryptophyl]-L-methionyl]-β-alanine

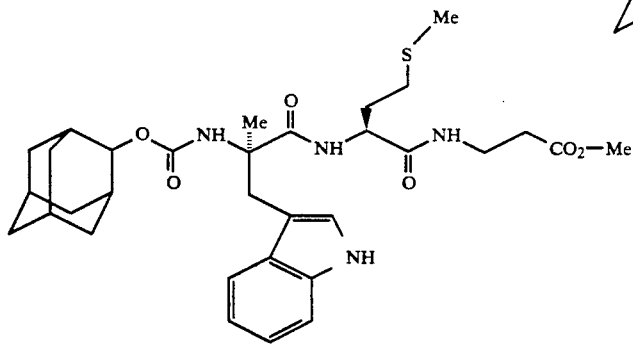

To a stirred solution of 1-hydroxybenzotriazole monohydrate (0.082 g, 0.54 mmol) and the acid (0.225 g, 0.43 mmol) in EtOAc (25 mL) was added N,N'-dicyclohexylcarbodiimide (0.098 g, 0.47 mmol) and the mixture stirred for 1 hour at room temperature. This was followed by β-alanine methyl ester hydrochloride (0.098 g, 0.71 mmol) and triethylamine (0.099 mL, 0.71 mmol) and the mixture stirred at room temperature for 48 hours. The N,N'-dicyclohexylurea was filtered off and the EtOAc washed with aqueous 5% citric acid solution (2×25 mL), saturated NaHCO₃ (2×25 mL), 5% citric acid (25 mL), and brine (25 mL). The EtOAc was dried over MgSO₄, filtered, and the solvent removed in vacuo. The residue was purified by chromatography over silica using 50% n-hexane/50% EtOAc then 33% n-hexane (67% EtOAc as eluant, giving the product as a white solid (0.168 g, 64%), m.p. 95°-102° C.; $[\alpha]_D^{20}$ +17.3° (c=.13 CHCl₃); IR (film) 3325, 1737, 1694, and 1657 cm⁻¹; NMR (CDCl₃) 1.49 (3H, s), 1.54-2.04 (19H, m), 2.26-2.41 (2H, m), 2.53-2.60 (2, m), 3.42-3.56 (4H, m), 3.67 (3H, s), 4.40-4.59 (1H, m), 4.81, 4.87 (1H, 2s), 5.08, 5.27 (1H, 2s), 6.99 (1H, d, J 2.3Hz), 7.08-7.38 (5H, m), 7.59 (1H, d, J 7.9Hz), 8.23 (1H, 2s); Anal. (C₃₂H₄₄N₄O₆S), C, H, N, S.

Step 4

To a stirred solution of the methyl ester (0.113 g, 0.19 mmol) in THF (10 mL) at 0° C. was added dropwise aqueous 0.1N LiOH solution (2.1 mL, 0.21 mmol) over 1 hour. The cold solution was stirred for 2 hours and then at room temperature for 24 hours. The solvent was removed in vacuo and the residue diluted with water (10 mL) and extracted with Et₂O (2×25 mL). The aqueous solution was made pH 4 with 0.1N HCl solution and extracted with EtOAc (2×25 mL). The combined EtOAc extracts were dried over MgSO₄, filtered, and the solvent removed in vacuo, giving the product as a white solid (0.082 g, 74%), m.p. 106°-117° C.; $[\alpha]_D^{20}$ +53° (c =0.10, CHCl₃); IR (film) 3310, 1694, and 1660 cm⁻¹; NMR (CDCl₃) 1.48-1.59 (5H, m), 1.71-2.03 (15H, m), 2.52

Example 14

S-methyl-N-[α-methyl-N-[(tricyclo3.3.1.1³,⁷]dec-2-yloxy)carbonyl]-D-tryptophyl-D-cysteine

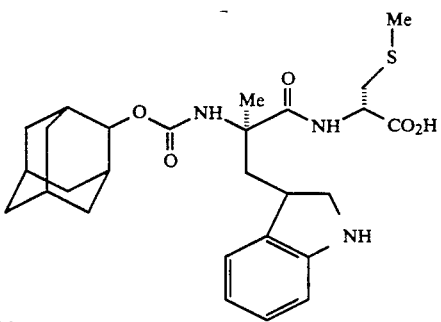

Step 1

Methyl S-methyl-N-[α-methyl-N-[(tricyclo[3.3.1.1³,⁷]dec-2-yloxy)carbonyl]-D-tryptophyl]-L-cysteine

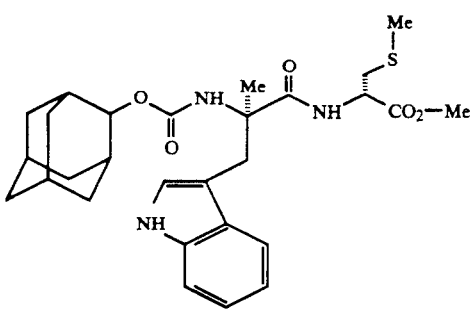

N,N'-dicyclohexylcarbodiimide (0.572 g, 2.77 mmol) was added to a stirred solution of 1-hydroxybenzotriazole monohydrate (0.483 g, 3.15 mmol) and the acid (1.0 g, 2.52 mmol) in EtOAc (100 mL) at room temperature. After 1 hour s-methyl-s-cysteine (0.585 g, 3.12 mmol) was added followed by dropwise addition of a solution of Et₃N (0.435 mL, 3.12 mmol) in EtOAc (25 mL) over 50 minutes. The mixture was stirred at room temperature for 48 hours, filtered, and the EtOAc solution washed with aqueous 5% citric acid solution (2×50 mL), saturated NaHCO₃ (2×50 mL), 5% citric acid solution (50 mL), and brine (50 mL). The EtOAc was dried over MgSO₄, filtered, and the solvent removed in vacuo. The residue was purified by chromatography over silica using 50% n-hexane/50% EtOAc as eluant, giving the product (0.955 g, 72%) as a white solid, m.p. 68°–75° C.; [α]$_D^{20}$+46.1° (c=0.23, CHCl₃); IR (film) 3358, 1743, 1700, and 1667 cm⁻¹; NMR (CDCl₃) 1.50–2.02 (17H, m), 2.05 (3H, s), 2.82 2.93 (2H, m), 3.32 (1H, d, J 14.7Hz), 3.53 (1H, d, J 14.7Hz), 3.73 (3H, s), 4.72–4.78 (1H, m), 4.84 (1H, s), 5.22 (1H, bs), 7.07–7.21 (4H, m), 7.37 (1H, d, J 8.0Hz), 7.60 (1H, d, 7.8Hz), 8.21 (1H, s); Anal. (C₂₈H₃₇N₃O₅S), C, H, N, S.

Step 2

To a stirred solution of the methyl ester (0.88 g, 1.67 mmol) in THF 990 mL) at 0° C. was added dropwise over 1.5 hours an aqueous 0.1N LiOH solution (18.4 mL, 1.84 mmol). The cold solution was stirred for 1 hour and then the solvent removed in vacuo. The residue was diluted with water (20 mL) and extracted with Et₂O (2×25 mL). The aqueous solution was acidified with 0.1N HCl solution (20 mL, 2 mmol) and extracted with EtOAc (2×50 mL). The EtOAc was dried over MgSO₄, filtered, and the solvent removed in vacuo, giving the product (0.676 g, 79%) as a white solid, m.p. 102°–107° C.; [α]$_D^{20}$+40° (c=0.10, CHCl₃); IR (film) 3344, 1713, and 1661 cm⁻¹; NMR (CDCl₃) 1.51–2.04 (20H, m), 2.84–2.99 (2H, m), 3.33 (1H, d, J 14.7Hz), 3.48 (1H, d, J 14.7Hz), 4.66–4.72 (1H, m), 4.86 (1H, s), 5.32–6.10 (2H, b), 7.02–7.19 (4H, m), 7.32 (1H, d, J 7.7Hz), 7.57 (1H, d, J 7.8hz), 8.48 (1H, s); Anal. (C₂₇H₃₅N₃O₅S), C, H, N, S.

Example 15

N-[α-Methyl-[N-[(tricyclo[3.3.1.1³,⁷]dec-2-yloxy)carbonyl]-D-tryptophyl]-ν-(methylsulfinyl)-L-α-aminobutanoic acid

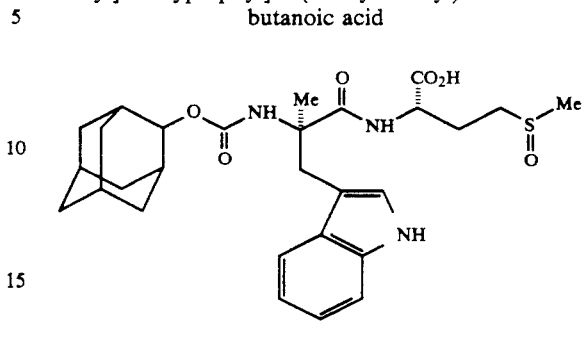

Step 1

S-methionine sulfoxide (0.90 g, 5.45 mmol) was added in one portion to a stirred solution of thionylchloride (0.791 mL, 10.9 mmol) in MeOH (25 mL) at 0° C. The cold solution was stirred for 1 hour then at reflux for 1 hour and overnight at room temperature. The solvent was removed in vacuo and the residue extracted into EtOAc (25 mL) and washed with saturated NaHCO₃ (10 mL). The aqueous layer was reextracted with EtOAc (2×25 mL), the aqueous solution evaporated to dryness, and triturated with EtOAc (25 mL). Removal of the solvent in vacuo gave the product (0.421 g, 43%) as a yellow syrup; IR (film) 1734 cm⁻¹; NMR (CDCl₃) 1.81 (2H, s), 1.91–2.04 (1H, m), 2.20–2.32 (1H, m), 2.59 (3H, s), 2.77–2.95 (2H, m), 3.58–3.64 (1H, m), 3.75 (3H, s); Anal. (C₆H₁₃NO₃S0.5H₂O), C, H, N, S.

Step 2

Methyl N-[α-methyl-N-[(tricyclo[3.3.1.1³,⁷]dec-2-yloxy)carbonyl D tryptophyl]-γ-(methylsulfinyl)-L-α-amino butanoate

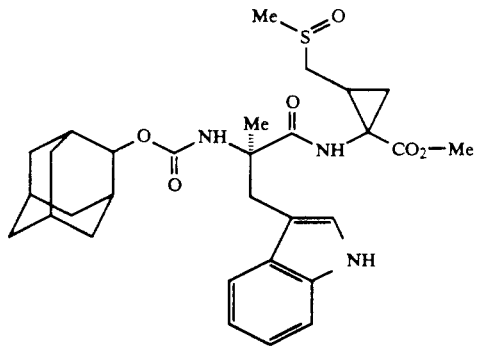

N,N'-dicyclohexylcarbodiimide (0.454 g, 2.20 μmol) was added to a stirred solution of 1-hydroxybenzotriazole monohydrate (0.368 g, 2.4 mmol) and the acid (0.793 g, 2.0 mmol) in EtOAc (75 mL) at room temperature. After 3 hours, the aminoester (0.40 g, 2.23 mmol) from Step 1 in anhydrous THF (25 mL) was added and the mixture stirred at room temperature for 4 days. The mixture was filtered and the organic solution washed with 5% citric acid (2×25 mL), saturated NaHCO₃ (2×25 mL), 5% citric acid (25 mL), and brine (25 mL). The EtOAc was dried over MgSO₄, filtered, and the solvent removed in vacuo. Purification of the residue by chromatography on silica using 2% MeOH/98% EtOAc then 5% MeOH/95% EtOAc as eluants gave the product (0.241 g, 22%) as a white solid, m.p. 117°-126° C.; IR (film) 3333, 1743, 1703, 1667, and 1050 cm$^{-1}$; NMR (CDCl$_3$) 1.51-1.55 (2H, m), 1.64-2.06 (16H, m), 2.33-2.41 (1H, m), 2.46-2.65 (5H, m), 3.30-3.44 (2H, m), 3.69 (3H, s), 4.52-4.62 (1H, m), 4.79 (1H, s), 5.37-5.42 (1H, m), 6.92-7.03 (1H, m), 7.06-7.20 (3H, m), 7.36 (1H, d, J 8.0Hz), 7.57-7.59 (1H, m), 8.31-8.37 (1H, m); Anal. (C$_{29}$H$_{39}$N$_3$O$_6$S0.5H$_2$O), C, H, N, S.

Step 3

To a stirred solution of the methyl ester (0.558 g, 1.0 mmol) in THF (60 mL) at 0° C. was added dropwise over 1 -our an aqueous 0.1N LiOH solution (11.0 mL, 1.1 mmol). The cold solution was stirred for 2 hours and the solvent removed in vacuo. The residue was diluted with water (15 mL) and extracted with Et$_2$O (2×25 mL). The aqueous solution was made pH 3 with 0.1N HCl solution and extracted with EtOAc (2×25 mL). The EtOAc solution was dried over MgSO$_4$, filtered, and the solvent removed in vacuo. The residue was purified by chromatography on reverse phase silica using 70% MeOH/30% water as eluant, giving the product (0.336 g, 62%) as a white solid; m.p. 129°-140° C.; IR (film) 3328, 1703, and 1670 cm$^{-1}$; NMR (DMSO-d$^6$) 1.38 (3H, s), 1.52-1.56 (2H, m), 1.74 2.18 (14H, m), 2.53 (3H, s), 2.60-2.74 (2H, m), 3.25 (1H, d, J 14.6Hz), 3.45 (1H, d, J 14.0H$_2$), 4.34 (1H, bs), 4.72 (1H, s), 6.88 (1H, bs), 6.95-7.00 (1H, m), 7.05-7.10 (2H, m), 7.36 (1H, d, J 7.9Hz), 7.54 (1H, d, J 7.8Hz), 7.98 (1H, b), 10.92 (1H, s), 12.84 (1H, b); Anal. (C$_{28}$H$_{37}$N$_3$O$_6$S).

Example 16

N-[α-methyl-N-[(tricyclo[3.3.1.1$^{3,7}$]dec-2-yloxy)carbonyl]-D-tryptophyl]-γ-(methylsulfonyl)-L-α-aminobutanoic acid

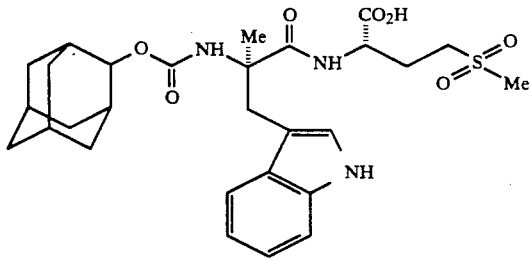

Step 1

S-methionine sulfone (0.85 g, 4.69 mmol) was added in one portion to a stirred solution of thionylchloride (0.681 mL, 9.38 mmol) in MeOH (25 mL) at 0° C. The cold solution was stirred for 2 hours and then heated at reflux for 2 hours, cooled and the solvent removed in vacuo. The residue was purified by recrystallization from MeOH which gave the product (0.673 g, 68%) as a white solid, m.p. 159°-166° C.; [α]$_D^{20}$ +12.3° (c=.20, MeOH); IR (film) 3410 and 1747 cm$^{-1}$; NMR (DMSO d$^6$) 2.28 (2H, dd, J 14.6, 7.4Hz), 3.02 (3H, s), 3.27-3.46 (2H, m), 3.76 (3H, s), 4.19 (1H, t, J 6.4Hz), 8.90 (3H, bs), Anal. (C$_6$H$_{14}$ClNO$_4$S), C, H, Cl, N, S.

Step 2

Methyl N-[α-methyl-N-[(tricyclo[3.3.1.1$^{3,7}$]dec-2-yloxy)carbonyl-D-tryptophyl]-γ-(methylsultonyl)-L-α-aminobutanoate N,N'-dicyclohexylcarbodiimide (0.504 g, 2.44 mmol) was added to a stirred solution of 1-hydroxybenzotriazole monohydrate (0.425 g, 2.78 mmol) and the acid (0.88 g, 2.22 mmol) in EtOAc (90 mL) at room temperature. After 2 hours s-methioninefultone methyl ester hydrochloride (0.616 g, 2.66 mmol) from Step 1 was added followed by dropwise addition over 10 minutes of a solution of Et$_3$N (0.371 mL) in EtOAc (10 mL). After stirring at room temperature for 19 hours the mixture was filtered and the solvent removed in vacuo. Purification of the residue by chromatography on silica using EtOAc as eluant gave the product (0.877 g, 69%) as a white solid recrystallized from EtOAc, m.p. 146.5-151° C.; [α]$_D^{20}$+14.2° (c=0.23, CHCl$_3$); IR (film) 3358, 1742, 1703, 1669, 1300, and 1131 cm$^{-1}$; NMR (CDCl$_3$) 1.51-2.10 (18H, m), 2.36-2.46 (1H, m), 2.82 (3H, s), 2.89-3.07 (2H, m), 3.26 (1H, d, J 14.7Hz), 3.40 (1H, d, J 14.7Hz), 3.68 (3H, s), 4.54-4.61 (1H, m), 4.78 (1H, s), 5.28 (1H, s), 6.79 (1H, d, J 7.4Hz), 7.06-7.19 (3H, m), 7.36 (1H, d, J 8.0Hz), 7.55 (1H, d, 7.8Hz), 8.36 (1H, s); Anal. (C$_{29}$H$_{39}$N$_3$O$_7$S0.25H$_2$O), C, H, N, S.

Step 3

To a stirred solution of the methyl ester (0.929 g, 1.62 mmol) from Step 2 in THF (100 mL) at 0° C. was added dropwise over 30 minutes an aqueous 0.1N LiOH solution (17.8 mL, 1.78 mmol). The cold solution was stirred for 2 hours and the solvent removed in vacuo. The residue was diluted with water (20 mL) and extracted with Et$_2$O (25 mL). The aqueous solution was acidified with 0.1N HCl solution (18 mL, 1.8 mmol) and extracted with EtOAc (2×25 mL). The combined EtOAc extracts were dried over MgSO$_4$, filtered, and the solvents removed in vacuo, giving the product (0.69 g, 76%) as a white solid, m.p. 133°-148° C.; [α]$_D^{20}$+17° (c=0.21, CHCl$_3$); IR (film) 3360, 1706, and 1671 cm$^{-1}$; NMR (DMSO-d$^6$) 1.34 (3H, s), 1 40-1.54 (2H, m), 1.73-2.26 (14H, m), 2.98 (3H, s), 3.20 (1H, d, J 14.6Hz), 3.35 (2H, br s), 3.44 (1H, d, J 14.4Hz), 4.34 (1H, br), 4.73 (1H, s), 6.94-7.08 (4H, m), 7.36 (1H, d, J 8.1Hz), 7.52 (1H, d, J 8.0Hz), 8.01 (1H, d, J 7.0Hz), 10.92 (1H, s), 12.61-13.00 (1H, br); Anal. (C$_{28}$H$_{37}$N$_3$O$_7$S0.4H$_2$O); C, H, N, S.

We claim:

1. A compound of formula

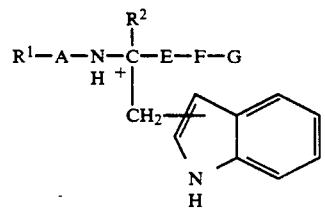

or a pharmaceutically acceptable salt thereof wherein:
R$^1$ is a cyclo- or polycycloalkyl hydrocarbon selected from

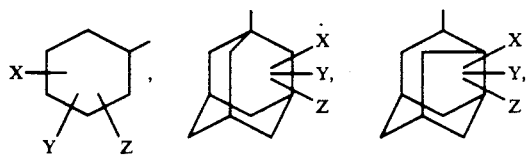

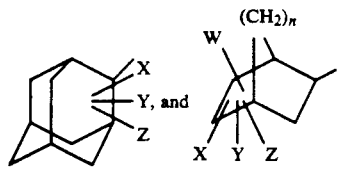

with from zero to four substituents, each independently selected from the group consisting of: a straight or branched alkyl of from one to six carbon atoms, halogen, CN, OR*, SR*, CO₂R*, CF₃, NR⁵R⁶, or —(CH₂)ₙOR⁵;, wherein R* is hydrogen, straight or branched alkyl of from one to six carbon atoms, R⁵ and R⁶ are each independently hydrogen or alkyl of form one to six carbon atoms; and n is an integer from zero to six;

A is —(CH₂)ₙCO—, —SO₂—, —SO—, —NHCO—,

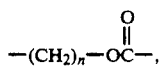

—SCO—, —O—(CH₂)ₙCO— or —HC═CH-CO— wherein n is an integer form zero to six;

R² is —CH₃, —CH₃CO₂H, —CH₂C≡CH;

E is —CONH—;

F is a bond or is a des-N form of alanine, substituted β-alanine, arginine, asparagine, aspartic acid, cysteine, glutamic acid, glutamine, glycine, isoleucine, leucine, lysine, methionine, serine, threonine, or valine;

G is OH, NH₂, —NHCOCH₂CH₂CO₂Y, —NHCOCH₂CH₂COCH₂C₆H₅, —NHCOCH₂CO₂Y, —NHCOCH═CHCO₂Y, —CH₂CO₂Y, —OCOCH₂CH₂CO₂H, —CH₂SCH₂CO₂H, —CH₂SCH₂CH₂CO₂H,

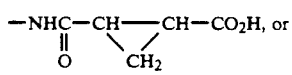

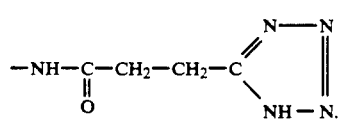

G cannot be hydrogen when F is a bond.

2. A compound according to claim 1 wherein the polycycloalkyl is selected from the group consisting of

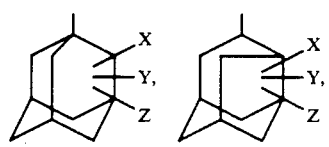

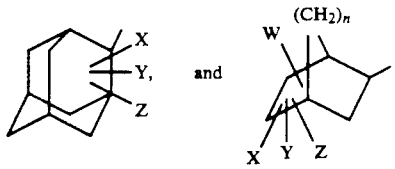

wherein W, X, Y, and Z are each independently hydrogen, a straight or branched alkyl of from one to six carbon atoms, CF₃, NR⁵R⁶, (CH₂)ₙCO₂R*, CN, F, Cl, Br, OR*, SR*, wherein R*, R⁵ and R⁶ are as defined in claim 1 and n is an integer of from 1 to 3.

3. A compound according to claim 1 wherein A is —NHCO—, OC(═O)—, —SO₂—, —S(═O)—, —SCO— or —CH₂CO—.

4. A compound according to claim 1 wherein

R¹ is 2-adamantyl or 1-(S)-2-endobornyl;

A is —NHCO—, —OCO—, —S02—, —S(═O)ₙ, —CH₂CO—;

R² is CH₃, —CH₂CO₂H, or —CH₂C≡CH;

E is —CONH—;

F is a des-N form of alanine, substituted β-alanine, arginine, asparagine, aspartic acid, cysteine, glutamic acid, glutamine, glycine, isoleucine, leucine, lysine, methionine, serine, threonine, or valine; and G is OH, NH₂, —NHCOCH₂CH₂CO₂H, —NHCOCH₂CH₂COCH₂C₆H₅, —NHCOCH₂CO₂H, —NHCOCH═CHCO₂H, —CH₂CO₂H, —OCOCH₂CH₂CO₂H, —CH₂SCH₂CO₂H, —CH₂SCH₂CH₂CO₂Y,

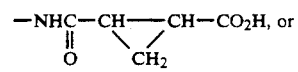

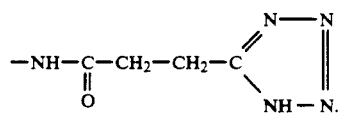

5. A compound according to claim 1 wherein:

R¹ is 2-adamantyl or 1-(S)-2-endobornyl;

A is —NHCO—, —OCO—, —SO₂—, —S(═O)— or —CH₂CO—;

R² is —CH₃, —CH₂CO₂H or —CH₂C≡CH;

E is CONH; and

F is CH(R)CO— wherein R is —CH₂CO₂H, —CH₂CH₂SCH₃, CH₂CH(CH₃)CH₃, —(CH₂)₃CH₃; and G is OH, NH₂, —NHCOCH₂CH₂CO₂H, —NHCOCH₂CH₂COCH₂C₆H₅, —NHCOCH₂CO₂H, —NHCOCH═CHCO₂H, —CH₂CO₂H, —OCOCH₂CH₂CO₂H, —CH₂SCH₂CO₂H, —CH₂SCH₂CH₂CO₂H,

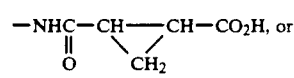

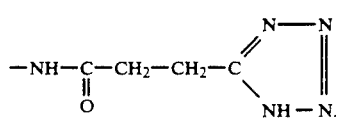

6. A compound named:

(R)-N-[3-(1H-indol-3-yl)-2-methyl-1-oxo-2-[[(tricyclo[3.3.1.1³,⁷]dec-2-yloxy)carbonyl]amino]-propyl]glycine, (R)-4-[[3-(1H-indol-3-yl)-2-methyl-1-oxo-2-[[(tricyclo[3.3.1.1³,⁷]dec-2-yloxy)carbonyl]amino]-propyl]amino]butanoic acid, Methyl (R)-4-[[3-(1H-indol-3-yl)-2-methyl-1-oxo-2-[[(tricyclo[3.3.1.1³,⁷]dec-2-yloxy)carbonyl]amino]-propyl]amino]butanoate, Phenylmethyl (R)-3-[[3-(1H-indol-3-yl)2-methyl-1-oxo-2 [[(tricyclo[3.3.1.1³,⁷]dec-2-yloxy)carbonyl]amino]-propyl]amino]propanoate, Methyl N-[α-methyl-N-[(tricyclo[3.3.1.1³,⁷]dec-2-yloxy)carbonyl]-D tryptophyl]-β-alanine, Phenylmethyl N-[2-methyl-N-[(tricyclo[3.3.1.1³,⁷]-dec-2-yloxy)carbonyl]-D-tryptophyl]glycine, N-[α-methyl-N-[(tricyclo[3.3.1.1³,⁷]dec-2-yloxy)-carbonyl]-D-tryptophyl]-β-alanine, Tricyclo[3.3.1.1³,⁷]dec-2-yl [1S-[1R*(S*),2R*]]-[2-[[1-(hydroxymethyl)-2-methyl-butyl]amino]-1-(1H-indol-3-ylmethyl)-1-methyl-2-oxoethyl]carbamate, Tricyclo[3.3.1.1³,⁷]dec-2 yl [R-(R*,S*)]-[2-[[1-(hydroxymethyl)-3-methylbutyl]amino]-1-(1H-indol-3-ylmethyl)-1-methyl-2-oxoethyl]carbamate, Methyl N-[α-methyl-N-[(tricyclo[3.3.1.1³,⁷]dec-2-yloxy)carbonyl]-D-tryptophyl]-L-methionine, N-[α-methyl-N-[(tricyclo[3.3.1.1³,⁷]dec-2yloxy)carbonyl]-D-tryptophyl]-L-methionine, and Methyl N-[N-[α-methyl-N-[(tricyclo[3.3.1.1³,⁷]dec-2-yloxy)carbonyl]-D-tryptophyl]-L-methionyl]-β-alanine.

7. A compound named
N-[S-methyl-N-[α-methyl-N-[(tricyclo[3.3.1.1³,⁷]dec-2-yloxy)carbonyl]-D-tryptophyl]-D-cysteinyl-β-alanine.

8. A compound named
S-methyl-N-[α-methyl-N-[(tricyclo[3.3.1.1³,⁷]dec-2-yloxy)carbonyl]-D-tryptophyl-D-cysteine.

9. A compound named
N-[α-Methyl-[N-[(tricyclo[3.3.1.1³,⁷] dec-2-yloxy)carbonyl]-D-tryptophyl]-γ-(methylsulfinyl)-L-α-aminobutanoic acid.

10. A compound named
N-[α-methyl-N-[(tricyclo[3.3.1.1³,⁷]-dec-2-yloxy)carbonyl]-D-tryptophyl]-γ-(methylsulfonyl)-L-α-aminobutanoic acid.

11. A pharmaceutical composition comprising an amount of a compound according to claim 1, effective to suppress the appetite, reduce gastric acid secretion, reduce anxiety, treat gastrointestinal ulcers, treat psychotic behavior, treat and/or prevent panic, block the reaction caused by the withdrawal form drug or alcohol use, potentiate the effects of morphine and other opioids in treating pain in a mammal, and a pharmaceutically acceptable carrier.

* * * * *

UNITED STATES PATENT AND TRADEMARK OFFICE
CERTIFICATE OF CORRECTION

PATENT NO. : 5,264,419　　　　　　　　　　　　　　Page 1 of 2
DATED : November 23, 1993
INVENTOR(S) : Horwell et al.

It is certified that error appears in the above-indentified patent and that said Letters Patent is hereby corrected as shown below:

Column 35, line 24, delete "form" and insert instead "from".

Column 35, line 30, "O" should be over the "O" and not over the "C".

Column 35, line 34, delete "form" and insert instead "from".

Column 35, line 42, delete "Y" and insert instead "H".

Column 35, line 43, delete "Y" and insert instead "H".

Column 35, line 44, delete "Y" two times and insert instead "H" two times.

Column 36, line 12, insert "-" before "$(CH_2)_n$".

Column 36, line 22, insert "-" before "$CH_3$" and delete "=" and insert instead "≡".

Column 36, line 32, delete "Y" and insert instead "H".

UNITED STATES PATENT AND TRADEMARK OFFICE
CERTIFICATE OF CORRECTION

PATENT NO. : 5,264,419
DATED : November 23, 1993
INVENTOR(S) : Horwell et al

It is certified that error appears in the above-indentified patent and that said Letters Patent is hereby corrected as shown below:

Column 37, line 22, insert "-" between "2" and "yl".

Column 37, line 27, insert "-" between "2" and "yloxy)".

Signed and Sealed this

Eleventh Day of April, 1995

Attest:

BRUCE LEHMAN

*Attesting Officer*      *Commissioner of Patents and Trademarks*